United States Patent
Cao et al.

(10) Patent No.: US 11,488,717 B2
(45) Date of Patent: Nov. 1, 2022

(54) METHOD AND SYSTEM FOR ANALYSIS OF SPINE ANATOMY AND SPINE DISEASE

(71) Applicant: Theseus AI, Inc., Santa Monica, CA (US)

(72) Inventors: Billy Cao, San Francisco, CA (US); Dave Harrison, San Francisco, CA (US); Luke Macyszyn, Los Angeles, CA (US); Sam Elhag, Los Angeles, CA (US)

(73) Assignee: Theseus AI, Inc., Los Angeles, CA (US)

( * ) Notice: Subject to any disclaimer, the term of this patent is extended or adjusted under 35 U.S.C. 154(b) by 371 days.

(21) Appl. No.: 16/878,533

(22) Filed: May 19, 2020

(65) Prior Publication Data

US 2020/0373013 A1 Nov. 26, 2020

Related U.S. Application Data

(60) Provisional application No. 62/851,602, filed on May 22, 2019, provisional application No. 62/894,818, (Continued)

(51) Int. Cl.
*G06K 9/00* (2022.01)
*G16H 50/20* (2018.01)
(Continued)

(52) U.S. Cl.
CPC ........... *G16H 50/20* (2018.01); *G06T 7/0016* (2013.01); *G06T 7/11* (2017.01); *G06V 10/26* (2022.01);
(Continued)

(58) Field of Classification Search
CPC ............ G06V 30/18; G06V 2201/033; G06V 10/25–273; G06V 20/49; G06V 20/695; G06V 40/162; G06V 20/80; G06V 20/698; G06V 10/764; G06V 10/44; G06V 2201/03; G06T 7/0014; G06T 2207/30012; G06T 2207/30008; G06T 7/10–194;
(Continued)

(56) References Cited

U.S. PATENT DOCUMENTS

| 6,021,213 A * | 2/2000 | Helterbrand ............ G06T 7/155 382/128 |
| 9,020,235 B2 | 4/2015 | Krishnan et al. |

(Continued)

OTHER PUBLICATIONS

International Search Report for PCT Application No. PCT/US2020/033659, dated Aug. 8, 2020.
(Continued)

*Primary Examiner* — Atiba O Fitzpatrick
(74) *Attorney, Agent, or Firm* — Clause Eight; Michael Catania

(57) ABSTRACT

A method for analysis of spine anatomy and stenosis is disclosed herein. The method includes preprocessing (3203) of images and then running segmentation models for each area of interest such as the foramen, disc, canal, vertebra (3206). In image post processing (3207), the system runs various heuristics to ensure accuracy (3208), computes areas (3209), and then runs a comparison model (3210). The report template produces HTML that is then converted to a PDF file of the final report (3214).

17 Claims, 27 Drawing Sheets

Related U.S. Application Data filed on Sep. 1, 2019, provisional application No. 62/960,149, filed on Jan. 13, 2020.

(51) Int. Cl.
| | |
|---|---|
| *G16H 10/60* | (2018.01) |
| *G16H 30/20* | (2018.01) |
| *G16H 30/40* | (2018.01) |
| *G16H 50/70* | (2018.01) |
| *G16H 50/30* | (2018.01) |
| *G16H 20/30* | (2018.01) |
| *G06T 7/11* | (2017.01) |
| *G06T 7/00* | (2017.01) |
| *G16H 20/40* | (2018.01) |
| *G06V 10/26* | (2022.01) |

(52) U.S. Cl.
CPC .............. *G16H 10/60* (2018.01); *G16H 20/30* (2018.01); *G16H 20/40* (2018.01); *G16H 30/20* (2018.01); *G16H 30/40* (2018.01); *G16H 50/30* (2018.01); *G16H 50/70* (2018.01); *G06T 2207/20081* (2013.01); *G06T 2207/20084* (2013.01); *G06T 2207/30012* (2013.01); *G06V 2201/033* (2022.01)

(58) Field of Classification Search
CPC ......... G06T 2207/20112; G06T 7/0012–0016; G06T 2207/30004–30104; G06T 2207/10072–10128; A61B 5/407; A61B 5/4566; A61B 5/4504; A61B 5/7485; A61B 6/469; G06K 9/6224; G16H 50/20; G16H 30/20; G16H 50/30; G16H 50/70; G16H 30/40

See application file for complete search history.

(56) References Cited

U.S. PATENT DOCUMENTS

| | | | |
|---|---|---|---|
| 9,317,926 B2 | 4/2016 | Wang et al. | |
| 9,940,711 B2 | 4/2018 | Bregman-Amitai et al. | |
| 10,039,513 B2 | 8/2018 | Bregman-Amitai et al. | |
| 10,111,637 B2 | 10/2018 | Bregman-Amitai et al. | |
| 10,140,543 B2 | 11/2018 | Dong et al. | |
| 2007/0223799 A1 | 9/2007 | Weiss | |
| 2012/0143090 A1* | 6/2012 | Hay | A61B 6/505 600/587 |
| 2014/0341457 A1* | 11/2014 | Weiss | A61B 5/0042 382/131 |
| 2015/0248593 A1* | 9/2015 | Nakashima | G06T 7/0012 382/131 |
| 2016/0073948 A1 | 3/2016 | Videman | |
| 2017/0148185 A1* | 5/2017 | Wu | A61B 5/4566 |
| 2018/0061048 A1 | 3/2018 | Weiss | |
| 2018/0140245 A1* | 5/2018 | Videman | A61B 5/103 |
| 2019/0274575 A1* | 9/2019 | Kim | G06T 7/0012 |
| 2021/0233237 A1* | 7/2021 | Kim | G06V 10/44 |

OTHER PUBLICATIONS

Written Opinion for PCT Application No. PCT/US2020/033659, dated Aug. 17, 2020.

Azimi et al.. Lumbar Spinal Canal Stenosis Classification Criteria: A New Tool, Asian Spine Journal, 2015;9 (3):399-406, Sep. 3, 2015.

* cited by examiner

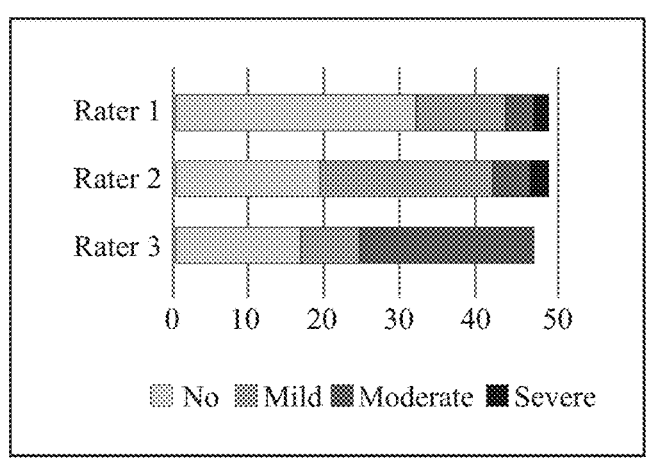
Radiologist evaluations for the same images vary, influencing false positives for surgery.
FIG. 3
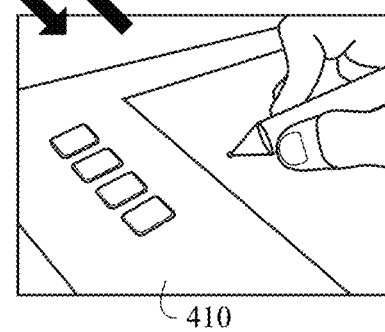
FIG. 4
PRIOR ART

|  | <20th Percentile | <20th - 39th Percentile | <40th - 59th Percentile | <60th - 79th Percentile | <80th - 99th Percentile | % of similar patients who had surgery |
|---|---|---|---|---|---|---|
| L1/2 | <158mm² | 159mm²-164mm² | 159mm²-164mm² | 159mm²-164mm² | 159mm²-164mm² | 8% |
| L2/3 | <158mm² | 159mm²-164mm² (!) | 159mm²-164mm² | 159mm²-164mm² | 159mm²-164mm² | 32% |
| L3/4 | <158mm² | 159mm²-164mm² | 159mm²-164mm² | 159mm²-164mm² | 159mm²-164mm² | 3% |
| L4/5 | <158mm² | 159mm²-164mm² | 159mm²-164mm² | 159mm²-164mm² (✓) | 159mm²-164mm² | 3% |
| L5/1 | <158mm² (!) | 159mm²-164mm² | 159mm²-164mm² (✓) | 159mm²-164mm² | 159mm²-164mm² | 57% |

DEMOGRAPHIC PERCENTILE
COMPARED TO MEN AGES 30-39

1800

| | <20th PERCENTILE | 20th - 39th PERCENTILE | 40th - 59th PERCENTILE | 60th - 79th PERCENTILE | 80th - 99th PERCENTILE |
|---|---|---|---|---|---|
| | SURGICAL CANDIDATE | | NOT A SURGICAL CANDIDATE | | |
| L1-L | <158mm$^2$ | 158-164mm$^2$ | 164-168mm$^2$ | 168-173mm$^2$ | 173-180mm$^2$ |
| L2-L | <132mm$^2$ | 132-140mm$^2$ | 140-144mm$^2$ | 145-150mm$^2$ | 150-160mm$^2$ |
| L3-L | <142mm$^2$ | 142-145mm$^2$ | 144-148mm$^2$ | 148-152mm$^2$ | 152-160mm$^2$ |
| L4-L | <94mm$^2$ | 94-100mm$^2$ | 100-106mm$^2$ | 106-112mm$^2$ | 112-124mm$^2$ |
| L5-L | <147mm$^2$ | 147-154mm$^2$ | 154-158mm$^2$ | 158-164mm$^2$ | 164-170mm$^2$ |
| L1-R | <158mm$^2$ | 158-164mm$^2$ | 164-168mm$^2$ | 168-173mm$^2$ | 173-180mm$^2$ |
| L2-R | <132mm$^2$ | 132-140mm$^2$ | 140-144mm$^2$ | 145-150mm$^2$ | 150-160mm$^2$ |
| L3-R | <142mm$^2$ | 142-145mm$^2$ | 145-148mm$^2$ | 148-152mm$^2$ | 152-160mm$^2$ |
| L4-R | <94mm$^2$ | 94-100mm$^2$ | 100-106mm$^2$ | 106-112mm$^2$ | 112-124mm$^2$ |
| L5-R | <94mm$^2$ | 147-154mm$^2$ | 154-158mm$^2$ | 158-164mm$^2$ | 164-170mm$^2$ |
| Improved VAS Score after 24mos | 82% | 74% | 39% | 26% | 16% |

FIG. 18

METHOD AND SYSTEM FOR ANALYSIS OF SPINE ANATOMY AND SPINE DISEASE

CROSS REFERENCES TO RELATED APPLICATIONS

The Present Application claims priority to U.S. Provisional Patent Application 62/851,602, filed on May 22, 2019, U.S. Provisional Patent Application 62/894,818, filed on Sep. 1, 2019, and U.S. Provisional Patent Application 62/960,149, filed on Jan. 13, 2020, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to analyzing spinal anatomy, diagnosing spinal stenosis, and recommending treatments for back pain.

Description of the Related Art

Spinal surgeries represent a sizeable proportion of the total cost of treatments for back pain and neck pain. However, methods for recommending spinal surgery vary widely. These variations reflect a lack of professional consensus in recommending spinal surgery. Moreover, evidence suggests many spinal surgeries have limited long-term effectiveness, meaning patients are incurring unnecessary expense and risk. Therefore, reducing the number of unnecessary spine surgeries is important for improving patient safety, patient outcomes, and healthcare efficiency. Proper patient referral and selection is expected to improve the outcome of spinal surgery. Additionally, referrals today can be slow and inefficient due to delays in manual review of imaging and treating patients on a 'first come first served' basis resulting in a poor overall patient experience.

Vertebra, discs, neural foramina, and spinal canals are critical structures in the spine.

Studies show that interpretations of spine MRIs by radiologists, physicians, and surgeons vary widely.

This contributes to high variability in patient management strategies, treatments, and outcomes.

This represents a large problem with over $100 billion spent annually on back pain. More than 250,000 surgeries happen each year that do not improve patient quality of life. In the United States, patients wait an average of 24 days to see a spine surgeon only to be redirected to more conservative therapy 4 out of 5 times. In Canada, the wait time for surgical consultations can be upwards of 40 weeks.

In many cases insurance providers or health systems mandate that patients go through cycles of pain medication, physical therapy, or spinal injections before even receiving a surgical consult. Sometimes these treatments can be more costly than a routine surgery that might alleviate pain.

According to the European Spine Journal, "Proper patient referral and selection is expected to improve the outcome of spinal surgery but no classification system currently exists that is supported by sufficient evidence to be broadly implemented."

This technology allows for the ability to analyze tens of thousands of patient MRIs to generate objective data that helps better diagnose and treat patients with back pain and neck.

BRIEF SUMMARY OF THE INVENTION

The present invention processes digital images of a patient's spine to form a supplemental report relating to spinal stenosis and back pain.

The present invention receives a digital image or image series of the patient's spine. The present invention applies image analysis algorithms to determine various measurements of spinal anatomy. The present invention compares these measurements, optionally comparing measurement ratios within a patient's anatomy, and/or optionally comparing the measurements to those of a matched population sample. The present invention uses these measurements to form a report. Alternatively, the measurements, scores, or recommendations on the report could be available via an API, web interface, or other medium. The report is preferably provided for the patient's physician, radiologist, or other healthcare providers to assist in the diagnosis and treatment of spinal stenosis and back pain.

One aspect of the present invention is a method comprising pre-processing a spine image or image series. The method also includes modeling the spine images using an AI engine. The method also includes generating a plurality of model images of the spine. The method also includes segmenting each of the plurality of model images of the spine; computing an area for each of the plurality of model images of the spine. The method also includes measuring at least one spine feature accurately. The method also includes comparing the measurement to nearby measurements or a normal range. The method also includes providing a degree of narrowing.

Another aspect of the present invention is the automatic segmentation of anatomic areas of interest such as vertebra, discs, neural foramina, and spinal canals.

Another aspect of the present invention is the ability to measure and quantify points of interest such as cross sectional dimension of neural foramina and spinal canals.

Another aspect of the present invention is a method to statistically model the variation in the area of lumbar neural foramina and spinal canals in a large asymptomatic population.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 3 is a graph showing the opinions of stenosis severity by expert radiologists of the same patients.

FIG. 4 is an illustration of a software used by a physician to input image segmentations for training.

FIG. 16B is a table of data visualizations for each lumbar level.

FIG. 18 is an illustration of area comparison to norm values for a demographic including a recommendation threshold for surgical candidacy.

DETAILED DESCRIPTION OF THE INVENTION

General Definitions

Figure 1:
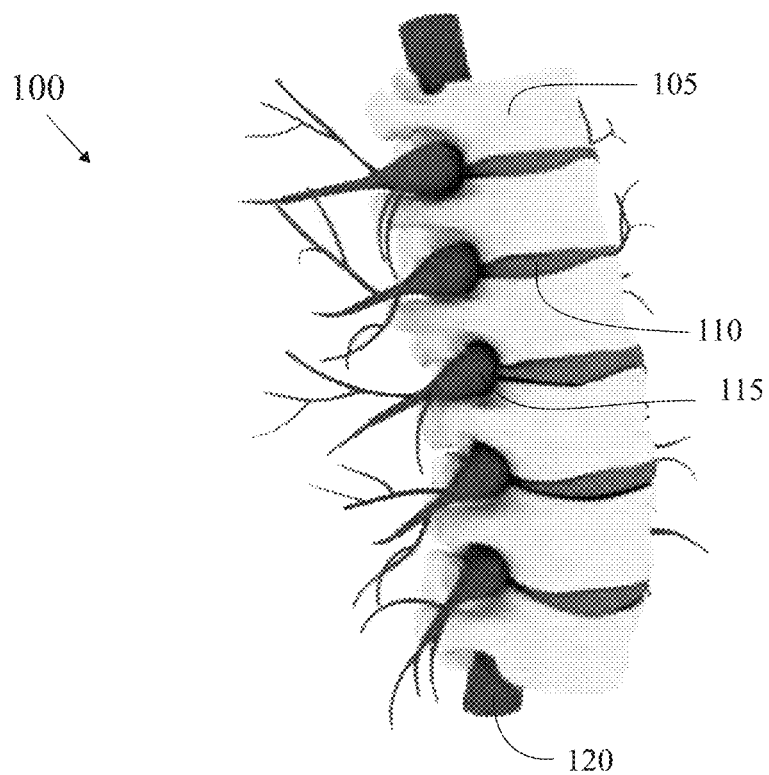
FIG. 1 is an illustration of a human spine focusing on the vertebrae, the discs, the foramen and the canal.

Adam optimizer is an extension to stochastic gradient descent optimization algorithm used in computer vision.

Axial view is a plane that divides the body into superior and inferior parts, roughly perpendicular to spine.

Canal or the spinal canal refers to the hollow passage formed by the foramen of the vertebrae through which the spinal cord runs.

Channel, in a U-Net, refers to multiple channels that comprise an image. For example, color images have standard RGB channels to indicate the amount of red, green, and blue. Input data with multiple channels require construction of a convolution kernel with the same number of input channels as the input data.

Convolutional layer—Convolutional layers are the major building blocks used in convolutional neural networks. A convolution is the simple application of a filter to an input that results in an activation. Repeated application of the same filter to an input results in a map of activations called a feature map, indicating the locations and strength of a detected feature in an input, such as an image.

Current Procedural Terminology (CPT) is a medical code set that is used to report medical, surgical, and diagnostic procedures and services to entities such as physicians, health insurance companies and accreditation organizations.

Dice score, or the Sçrensen-Dice coefficient, is a statistic used to gauge the similarity of two samples.

Discs or intervertebral discs throughout the spine act as shock absorbers, ligaments that hold the vertebrae together, and cartilaginous joints that allow slight mobility of the spine. There are twenty three vertebral discs in the spinal column.

Dlib is a modern C++ toolkit containing machine learning algorithms and tools for creating complex software.

Downsampling, or decimation, is the process of reducing the sampling rate of a signal.

Electronic Health Record (EHR) is a digital version of a patient's paper chart.

Ensemble of regression trees (ERT) is a predictive model composed of a weighted combination of multiple regression trees.

Foramen or foramina are the bony hollow archway created by pedicles of adjacent vertebrae, creating a passageway through which all spinal nerve roots run.

Max-pooling is a pooling operation that selects the maximum element from the region of the feature map covered by the filter. The output after max-pooling layer is a feature map containing the most prominent features of the previous feature map.

Patient Reported Outcome Measures (PROMS) are utilized to track patient health through a series of questions. Common PROMs include Visual Analogue Score (VAS), the EQ-5D from the EuroQol Group, or the Oswestry Disability Index (ODI).

Hausdorff distance is the longest distance you can be forced to travel by an adversary who chooses a point in one of the two sets, from where you then must travel to the other set. In other words, it is the greatest of all the distances from a point in one set to the closest point in the other set.

ICD-9 is the official system of assigning codes to diagnoses and procedures associated with hospital utilization in the United States.

Keras is a high-level neural networks API, written in Python and capable of running on top of TensorFlow, CNTK, or Theano.

Kernel, in a U-net for image processing, is a small matrix. It is used for blurring, sharpening, embossing, edge detection, and more. This is accomplished by doing a convolution between a kernel and an image.

Pixel in digital imaging is a physical point in a raster image or the smallest addressable element in an image or display device.

Sagittal view is a plane parallel to the sagittal suture. It divides the body into left and right.

Skip connections are extra connections between nodes in different layers of a neural network that skip one or more layers of nonlinear processing.

Stride, in a U-Net, denotes how many steps are moved with each step in a convolution.

Supervised Learning is the machine learning task of learning a function that maps an input to an output based on example input-output pairs. It infers a function from labeled training data consisting of a set of training examples.

Support Vector Machine (SVM) are supervised learning models with associated learning algorithms that analyze data used for classification and regression analysis.

TensorFlow is an open-source software library used for machine learning applications such as neural networks.

U-Net is a convolutional neural network that was developed for biomedical image segmentation at the Computer Science Department of the University of Freiburg, Germany. The network is based on the fully convolutional network and its architecture was modified and extended to work with fewer training images and to yield more precise segmentations.

Unit, in a U-Net, refers to the basic unit of computation in a neural network also known as a neuron or a node.

Vertebra are the series of small bones forming the backbone, having several projections for articulation and muscle attachment, and a hole through which the spinal cord passes.

Digital Imaging

The present invention retrieves a series of digital images of a patient's spine.

The image series is generated by any medical imaging means, including: Magnetic Resonance Imaging (MRI), ultrasound, X-ray, endoscopy, elastography, tactile imaging, thermography, medical photography, nuclear medicine, functional imaging techniques (fMRI), positron emission tomography (PET), single-photon emission computed tomography (SPECT), computed tomography (CT), and related means.

The images are encoded in any image format, including: DICOM, NIFTI, GIF, JPEG, PNG, BMP, or JPIP.

The images are preferably in two dimensions (2D). Alternatively, the images are in three dimensions (3D).

The images are preferably transmitted using the DICOM standard.

The spinal images preferably include the sagittal and axial views.

Anatomical Segmentation and Measurement

The present invention applies algorithms to segment and measure the patient's anatomy. The integrated segmentation model is trained through supervised learning using segmentations of spinal anatomy.

To train the spine segmentation model, a set of spine MR images are randomly chosen for algorithmic training purposes. Physicians segmented areas of interest including discs, foramen, canal, and vertebrae and these segmentations were used to train a Deep-U-Net model to segment disks on MR images.

Alternatively, the segmentation model is optionally trained using one of numerous other possible image segmentation neural networks such as DeepLab, a Regular FCN, or Mask R-CNN.

The Deep-U-Net is implemented by using the Keras application programming interface to the TensorFlow library. The U-Net contains four downsampling units, followed by a core unit, followed by four upsampling units, with skip connections between the respective downsampling and upsampling units. Each downsampling unit consists of a convolutional layer and a max-pooling layer. The convolutional layers preferably have a stride of 1 pixel and a kernel size of 3×3. The number of channels goes from 32 in the first downsampling layer to 64 in the second one, 128 in the third one, and 256 in the fourth one. The number of inputs goes from 256×256 in layer 1 to 32×32 in layer 4. The core unit is convolutional with 512 channels. The upsampling units consists of convolutional layers followed by upsampling layers to drive output sizes back from 32×32 to 256×256, which produces the final output. Rectified linear unit activation is used for convolutional neurons throughout the architecture, except the final output layer, which uses sigmoidal activation. The Deep-U-Net model provides a highly accurate detection and segmentation of intervertebral disks.

When an image or image series is provided, the present invention performs various pre-processing steps before attempting segmentation. Pre-processing comprises: resampling, bias correction, and pose correction, but many include a variety of other steps to prepare the image for automated segmentation. Before segmentation, MR images are resampled preferably to 256×256 pixels. A two-step approach is used to autonomously segment neural foramina. The first step is the detection step, and the second is the segmentation step. In the detection step, the present invention preferably detects a 25×25 pixel window containing the neural foramen. A support vector machine-based object detection system is trained by using histogram of oriented gradients (21) features and the hard negative mining paradigm to classify if a particular pixel window (preferably 25×25) contains a foramen. In the segmentation step, an ensemble of regression trees-based (22) shape regression model is used to delineate the foramen. Both the detection step using support vector machines and the delineation step using ensemble of regression trees are implemented by using the Dlib software library.

For the central canals, a hybrid machine learning model to execute segmentation is used. The first step preferably detects a 25×25 pixel window containing the canal. An ensemble of support vector machine (SVM)-based object detection systems is trained using histogram-of-oriented gradient features and the hard-negative mining paradigm to "classify" whether a particular 25×25 pixel window contains a central canal. The SVMs are linear SVMs, preferably with C=10, 50, 100, 150, 250, 500, 1000. A window classified by ≥4 SVMs as the spinal canal is preferably considered a "positive" detection. The image is cropped along this window and passed on to the second step of segmentation, which is executed using an ensemble of regression trees (ERT) shape-regression model. We used the ERT with v=0.05 and a tree depth set to 2 to predict 68 points, which form the contour of each spinal canal.

A Deep-U-Net model is trained on designated sagittal MR images to segment discs and is implemented using the Keras API running on top of TensorFlow 1.3.0, A rectified linear unit is used for convolutional neurons throughout the architecture except for the final output layer, which uses sigmoidal activation. The present invention preferably uses a fixed learning rate (1e-5) and the Adam optimizer with drop-out (probability of 0.25) regularization. The loss function used was the negative of the Dice score.

The Dice scores, the Hausdorff distance, and average surface distance metrics are used to compare overlaps for automatic spinal canal segmentations with segmentations generated by manual raters and manual raters among themselves to demonstrate the accuracy of the automatic measurements. As another measure of the value of automatic segmentation, human-driven segmentation of a spinal canal takes between 30 and 40 minutes for each image, while the most recent embodiment of the present invention's segmentation takes between 20 and 25 seconds.

The measurements of each area are optionally utilized to perform more advanced calculations such as intercomparisons within a given anatomical feature such as spinal canal or across features such as a canal to disc comparison. As an example, the canal area at a given level (e.g. L1) could be compared to the area of a nearby level (e.g. L2) to determine whether narrowing is present.

Those skilled in the art will recognize the precise numbers given here represent one embodiment of the present invention.

Comparison Population, Evaluative Scores, and Recommendations

The present invention compares measurements of the patient's spinal anatomy to average measurements from patients similar in one or more characteristics. For example, a given patient may be compared to demographically similar patients by age, height, and gender without related symptoms. This can be used to show whether a given patient's anatomical area or other combinatorial calculation based on multiple areas is below or above a normative range.

In order to build a normal population of measurements, a set of patient images is cross referenced with ICD-9 codes to eliminate diseases related to the presence of spinal pathology or symptoms attributable to the spine. In one embodiment, a 1,755 person population was built containing men and women, ages ranging from 19 to 81 years.

The final multivariable linear regression model was characterized by the equation:

$$\text{Neural foraminal area} = w_1(\text{age}) + w_2(\text{sex}) + w_3(\text{height}) + w_4(\text{height·sex}) + c,$$

which is fitted to the data. The symbol c is the intercept in the regression model. Each coefficient is analyzed to determine whether it is significantly related to the output variable, namely, the neural foraminal area. Age as well as height are significant predictors of neural foraminal areas. Neural foraminal areas correlated directly with patient height and inversely with patient age.

A similar statistical approach is used for the population model of the spinal canal.

The foramina and spinal canal areas of a given image with a given age, height, gender are compared to the population model to indicate standard deviations from the mean. Additionally, the patient demographics and measurements are compared to other patients to determine a percent likelihood of surgery as indicated by previous surgeries indicated in the EHR record by CPT code.

The axial MRIs containing segmented canals are cross-referenced with their sagittal MRIs containing segmented intervertebral discs to locate slices at each lumbar level in a standard way. At axial slices where the center of a disc was found, canal areas were documented so that they could be compared with respect to age, sex, and height.

In another embodiment, the patient's measurements are compared to a database of patients who exhibited similar symptoms to identify common treatments or treatments with positive outcomes. For example, the percentage of patients with similar measurements and symptoms who received a given treatment could be calculated. This is optionally expanded further to calculate the percentage of patients with similar measurements and symptoms who received a given treatment and reported a high level of satisfaction or reduced pain.

Outcomes measures utilized in the system include Patient Reported Outcome Measures (PROMS) or digital monitors such as a pedometer or an accelerometer equipped range of motion measurement. Common measurements taken before and after surgery include VAS, EQ5D, or ODI as well as distance able to walk without pain or other objective range of motion measurements. As new patient images are processed, these outcome measurements are optionally referenced as part of the large historical patient database to produce a recommendation.

Other characteristics from a patient intake form, electronic health record, digital health monitor, or other source are optionally used in the system to provide an overall score for a given treatment.

Several studies have shown correlations between various factors and whether a surgery was a success.

One example with a negative correlation to surgical success is BMI. Another is smoking.

On the other hand, more leg pain than back pain has been associated with positive outcomes.

These types of profile information or symptoms are optionally used in conjunction with the system measurements or independently and factored into an overall evaluative score or treatment recommendation. The evaluative score or recommendation for a given patient is optionally determined through a number of methods such as percentage of similar patients, simple statistical correlation, aggregation of a weighted set of features, or use of a nearest neighbor algorithm.

Report Contents

The present invention outputs a report showing spinal images, measurements, calculations related to those measurements, and results or insights from comparisons to a patient database containing data such as symptoms, demographics, treatments, and outcomes. The report optionally contains an evaluative score for the patient's spine, for a given anatomical area of the spine, for a rendered diagnosis, and for a treatment.

Spine image and patient demographic are utilized as the method for analysis of spine anatomy and degenerative disease including stenosis. Through direct upload or by integrating with an electronic health record and imaging archive, spine MRI studies in male and female populations of various ages and heights are retrieved. These images are anonymized and sent to a spine AI (artificial intelligence) model in the cloud (remote server).

Image annotation-customer report. A given image is then annotated via our software producing a new image that can be returned to the PACS (Picture Archiving and Communication System) for viewing by a radiologist or other physician. Additionally, an image is generated that shows the patient's measurement for lumbar foramina and canal, the standard deviations from the mean per the population model, and the percent likelihood of surgery as compared to like patients.

One embodiment is a structured reporting design/method for spine images (as comparisons to demographic data).

The report may contain select images of the patient's anatomy such as the canal, vertebrae, discs, or foramina. These images may be highlighted to show the segmentations performed. The images may also be annotated with raw measurements, intrapatient comparisons (e.g. 20% narrowing), and a standard deviation from the mean population.

The report optionally shows the patient's spinal measurements visually as a plot on a normal curve or box plot indicating where the measurements fall as compared to a normal range. Alternatively, these values could be displayed in a table.

The report optionally renders a severity of stenosis rating as a number value (e.g. 70% more stenotic as compared to a normal population) or as a mapped word value for a given range (e.g. severe stenosis) or as a visual representation (e.g. donut graph or bar graph).

In addition to stenosis, the report optionally renders additional diagnoses based on image biomarkers identified such as nerve impingement or degenerated disc.

Yet another embodiment is a system whose outputs are the percent likelihood of surgery based on a patient database. The report may contain a percentage (%) likelihood of a given treatment taking place and having a positive outcome reported based on historical treatments of like-patients in a database.

Yet another embodiment is a system whose outputs are percent likelihood of positive outcome with specific treatment based on patient database and reported measures: examples being (but not limited to) VAS, EQ5D, and ODI. The report may contain a percentage (%) likelihood of a given treatment (e.g. surgery, physical therapy, etc) taking place based on historical treatments of like-patients in a database.

Yet another embodiment is a system whose outputs are percent likelihood of positive outcome with specific treatment based on patient database and natural language processing of EHR.

The report optionally includes an evaluative score for a treatment. This score may be based on a single data point (e.g. % of similar patients who had surgery), an algorithm calculation (e.g. nearest neighbor) or a combination of weighted data points (e.g. % likelihood of similar patients who had surgery+(n)factors correlated with negative surgical outcomes).

An evaluative score for a diagnosis or treatment is optionally displayed in a visual or number form. For example, the report might indicate that surgery is 90% likely as a donut graph or bar graph.

The report optionally includes text insights based on patient traits such as "Patient BMI is >30 which has been found to have a negative impact on surgical outcome."

The report optionally allows user input to report errors, confirm results, or record decisions made or physician notes. This is optionally done through a link to an external system or form or directly in the interface. For example, a radiologist could scroll through an integrated image viewer on the report and confirm or report an error for a given image. Similarly, a primary care physician could indicate that the patient was referred to a physical therapist. These inputs would be recorded in a database for use in upgrading the report or underlying algorithms.

The report is optionally rendered as a PDF, Excel, Word Doc or in a live web interface or portal.

The data for the report is stored in a database and could be pulled or pushed to external systems via API, email or text, software platform notification, or other.

This is optionally utilized to more quickly triage patients to appropriate treatment. For example, a patient with a high confidence interval for success with physical therapy might be routed to a therapist via email notification rather than scheduled with a surgeon for consultation thereby expediting appropriate treatment.

Another embodiment is a system that does the segmentation, patient comparison, annotation, and sends back the report, a link to a report, or the raw data back to a PACS or EHR system.

The present invention is optionally integrated into a telemedicine system.

Figure 2:
FIG. 2 is a sagittal view of a human spine MRI.

As shown in FIG. 1, the vertebrae 105 align to form the vertebral spinal canal 120. The discs 110 sit between the vertebrae and bear weight. The foramen 115 are passages through which nerve roots run. Both the canal and foramen may narrow for various reasons causing nerve impingement or other damage resulting in pain and other symptoms that may prompt consideration of surgical intervention. FIG. 2 shows an example of this narrowing 200, also called spinal stenosis in the lumbar region. Specifically, there is clear narrowing at the L2/L3, L3/L4, and L4/L5 levels. This narrowing may be caused as part of the aging process by degenerative arthritis.

Studies show that interpretations of spine MRIs by radiologists, physicians, and surgeons vary widely. FIG. 3 shows results 300 from a research study in which three different radiologists rated the same set of spine MRIs. These raters identified the images as having a degree of stenosis as follows: no (stenosis), mild, moderate, and severe. As shown in the graph, raters varied widely in interpretation of the spine MRIs including rater one indicating no stenosis for many of the images and raters two and three showing significant disagreement between the frequency of moderate or mild stenosis. This high variability in interpretation contributes to high variability in patient management strategies, treatments, and outcomes. Since MRIs are the main diagnostic tool for determining surgical candidates and these ratings directly influence what patients will be evaluated and ultimately undergo surgical intervention, this is an important area for improvement.

Figure 5:
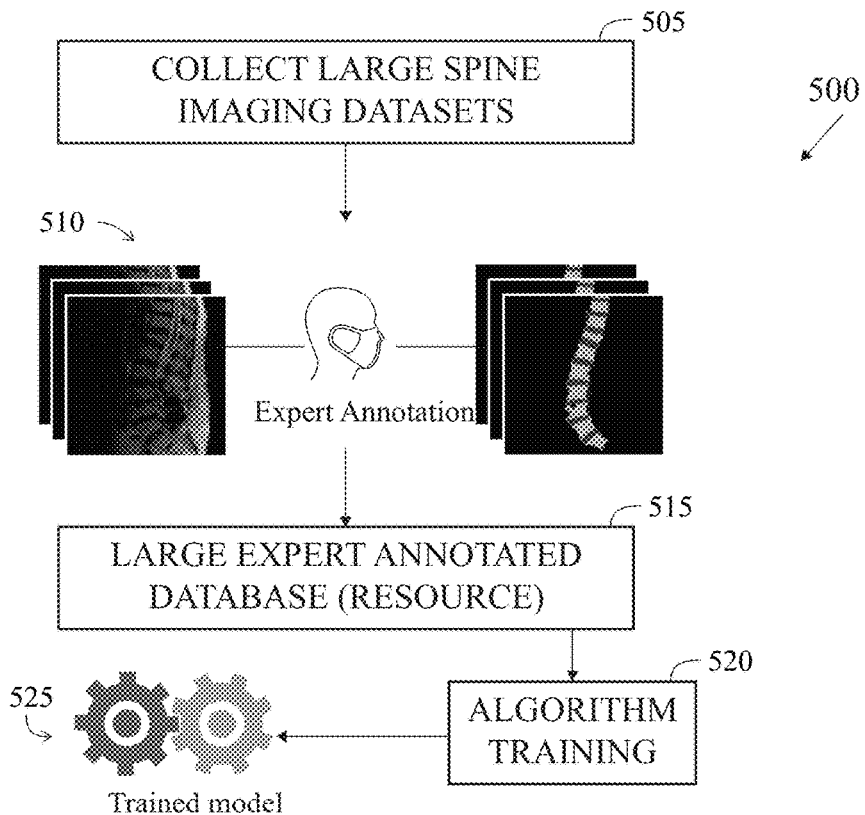
FIG. 5 is a block diagram for generating deep learning models of spine images.
Figure 6:
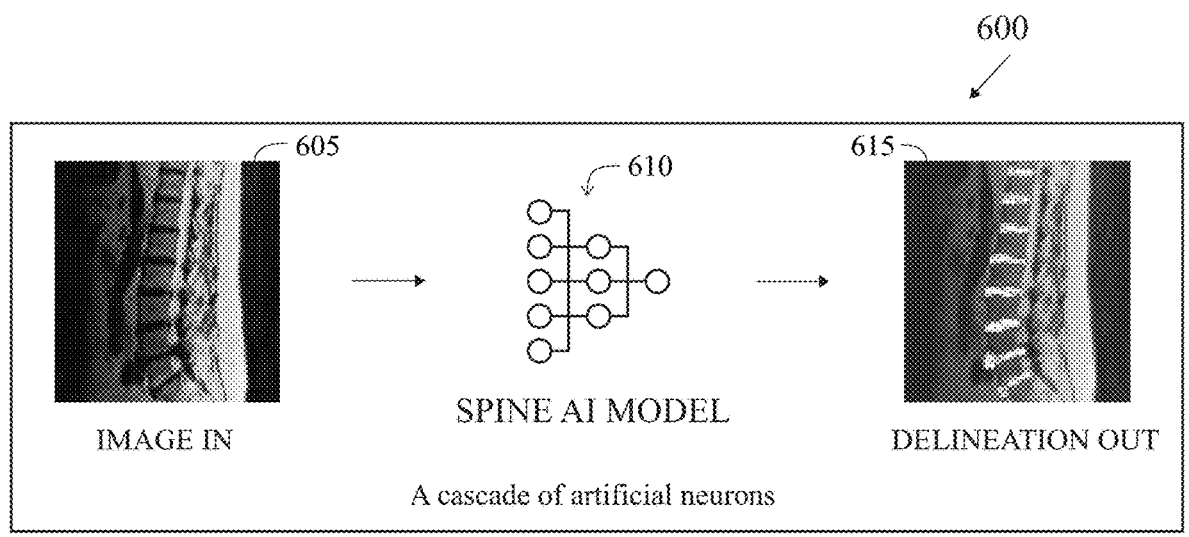
FIG. 6 is a high level depiction of a model that automatically segments specific areas of the spine.

In order to provide more consistent and accurate ratings, one would need to correctly identify the given anatomy and measure its area. FIG. 4 shows a tool called ITK-SNAP 400 that was used in conjunction with a WACOM table 410 by neuroradiologists to hand segment or outline 405 the key anatomy of the spine including the vertebrae, discs, foramina, and canal. Those familiar with the state of the art will note that a model could be trained in numerous ways based on various inputs. For instance, a model could be generated without human training that recognized borders of different anatomical areas or a model could be generated based on a combination of automatic identification of areas and human input on the accuracy of these identifications. FIG. 5 shows conceptually that a large imaging data set 505 can be combined with these expert segmentations/annotations 510 and advanced training methods 520 to generate a model 525 that will perform similar segmentations. A large dataset is required to validate the accuracy of the segmentations since diverse populations have differences in anatomical dimensions or shape. As another simple example, a patient's height impacts the anatomical area of the spine and number of slices produced in a specific MRI study. FIG. 6 shows the result of an adequately trained model 600. An image is run through the model 605, which then evaluates the image 610 and automatically segments the desired anatomy 615. In this example, the image shows automatic delineation of the discs in an axial view.

Figure 7:
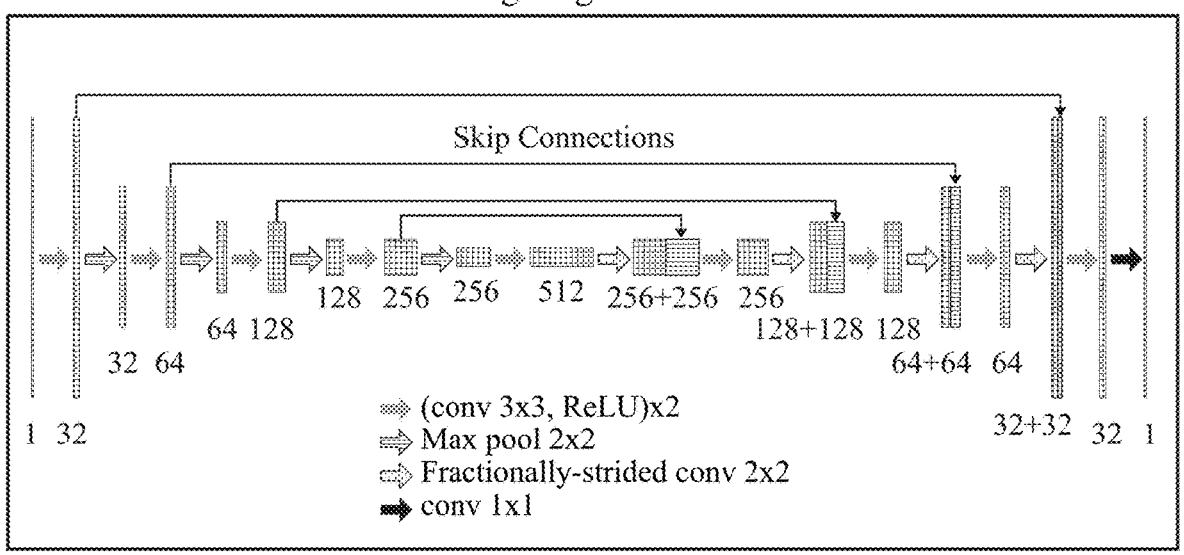
FIG. 7 is an illustration of a standard biomedical image segmentation network.

FIG. 7 depicts a u-net which is one method that could be used for biomedical image segmentation. A u-net supplements a usual contracting network by successive layers and utilizes upsampling operators.

Figure 8A:
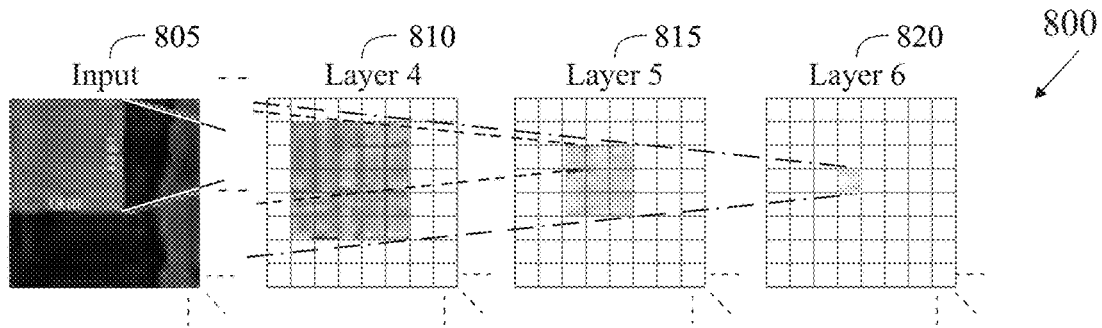
FIG. 8A is an illustration of a multi-scale network.
Figure 8B:
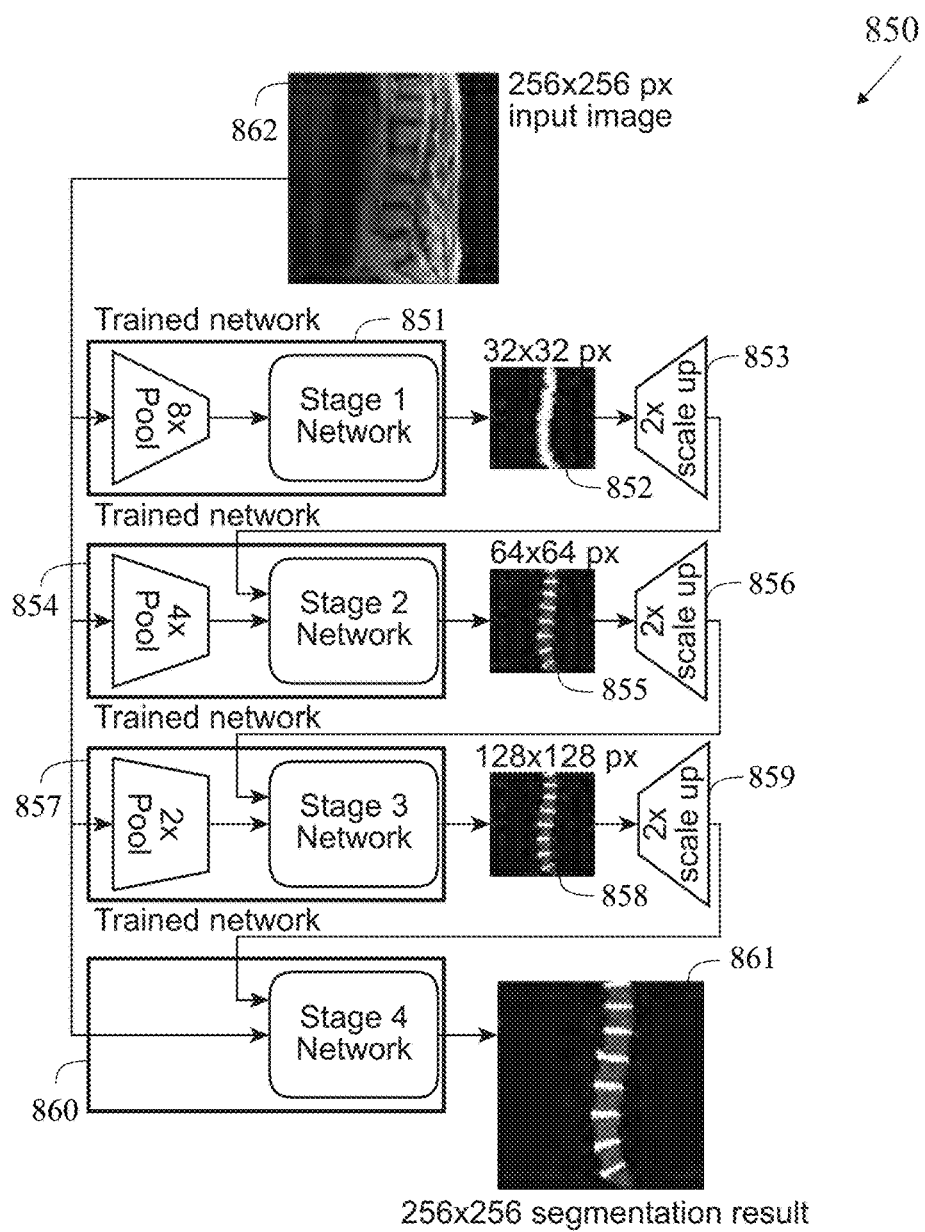
FIG. 8B is a flow chart of a multi-scale network.

FIG. 8 is an illustration of a multi-scale network.

Figure 9:
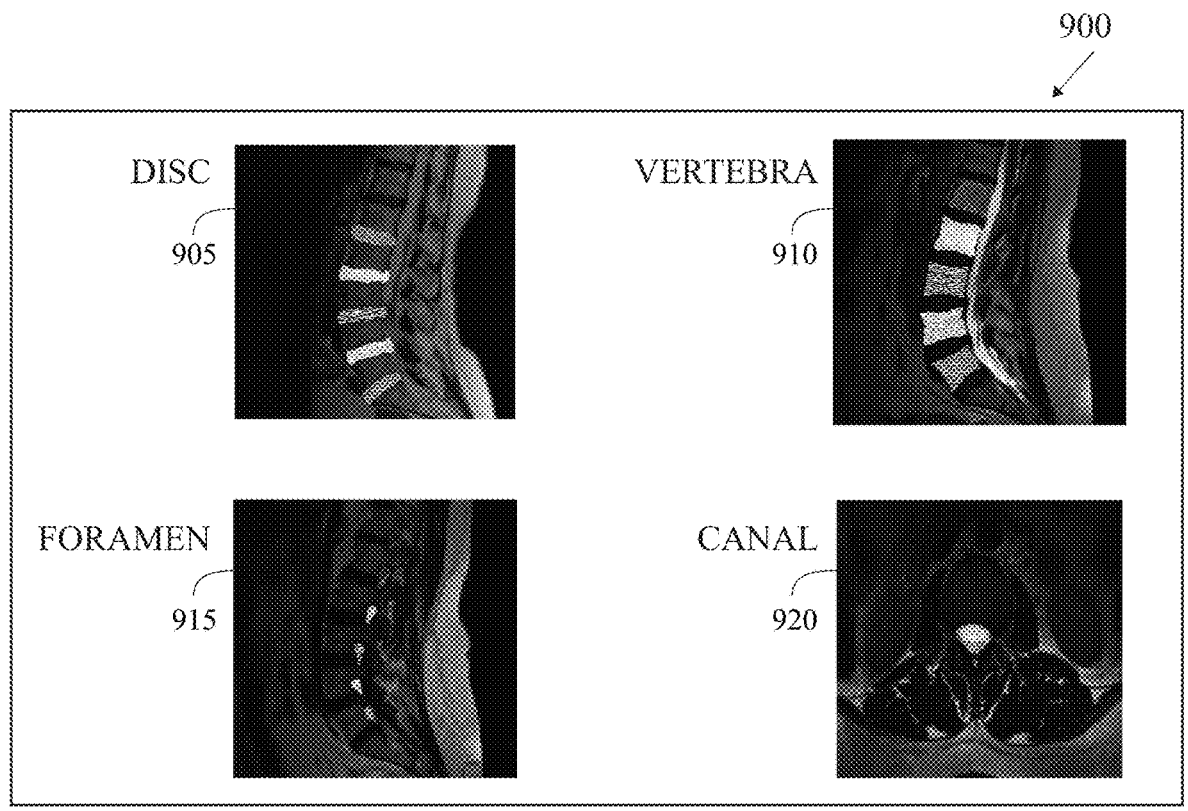
FIG. 9 illustrates images of disc, vertebra, canal and foramen that have been segmented and highlighted automatically.

FIG. 9 shows automatic segmentations highlighted 900 of each key spinal area: disc 905, vertebra 910, foramen 915, canal 920. The areas are highlighted so that a viewer can easily see them. Additionally, the highlighted segmentations can be used to compute an anatomical area measurement.

Figure 10:
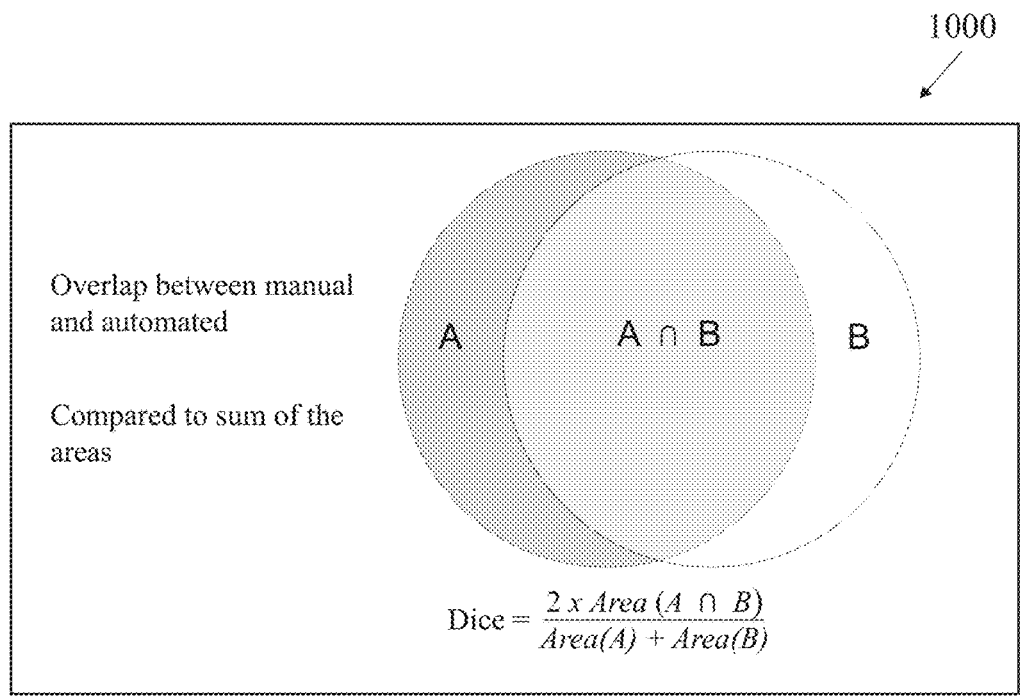
FIG. 10 is an illustration describing a dice score.

FIG. 10 describes a measure of accuracy called a Dice score or Sçrensen-Dice coefficient 1000. This measures the similarity of samples, in this case providing a gauge of the similarity between an automated segmentation performed by a trained model and manual segmentation of the anatomy performed by a radiologist. This measure could also be used to compare the similarity between two radiologist segmentation to provide a benchmark for an algorithmic model.

Figures 11A, 11B:
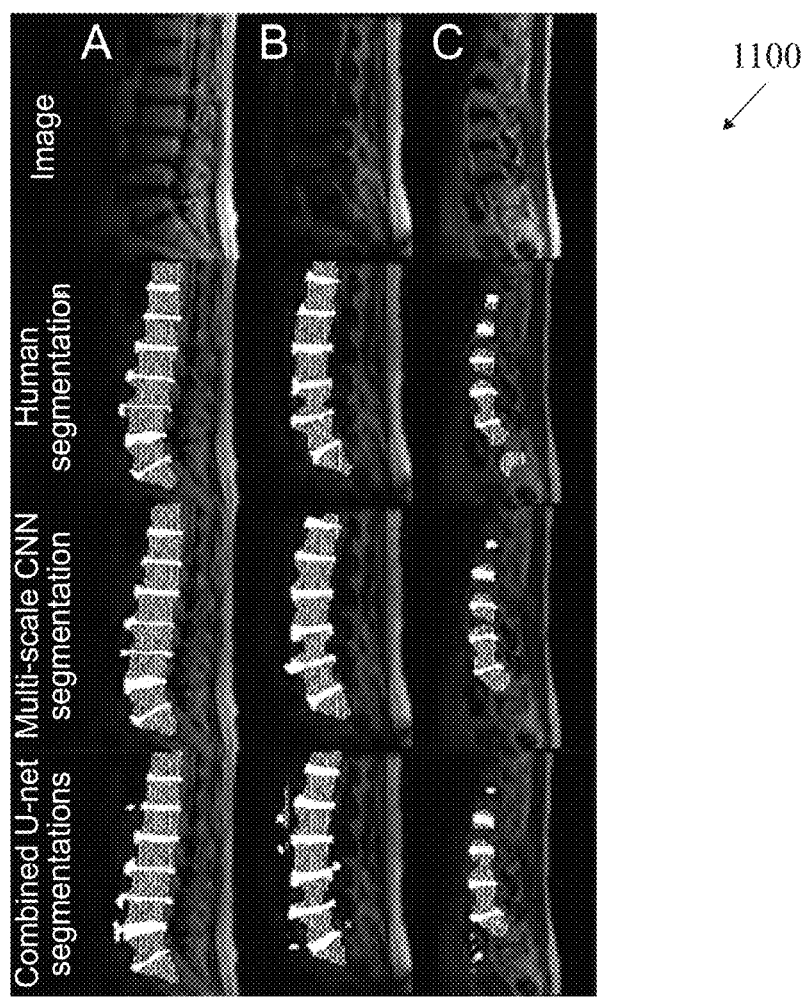
FIG. 11A is an illustration of images for combined U-net segmentations.
FIG. 11B is an illustration of dice scores for segmenting vertebrae and disks.

FIG. 11A compares the segmentation of three sagittal views of the spine by different methods 1100.

Figure 12A:
FIG. 12A is an illustration of dice scores for lumbar foramina.

FIG. 12A provides an example of foraminal segmentation 1200. In the image, the foramina of the five lower lumbar levels are clearly highlighted by a trained model. This may assist a reviewer in identifying the foramina or quantifying the level of stenosis. Additionally, the area of the highlighted pixels can be computed.

Figure 12B:
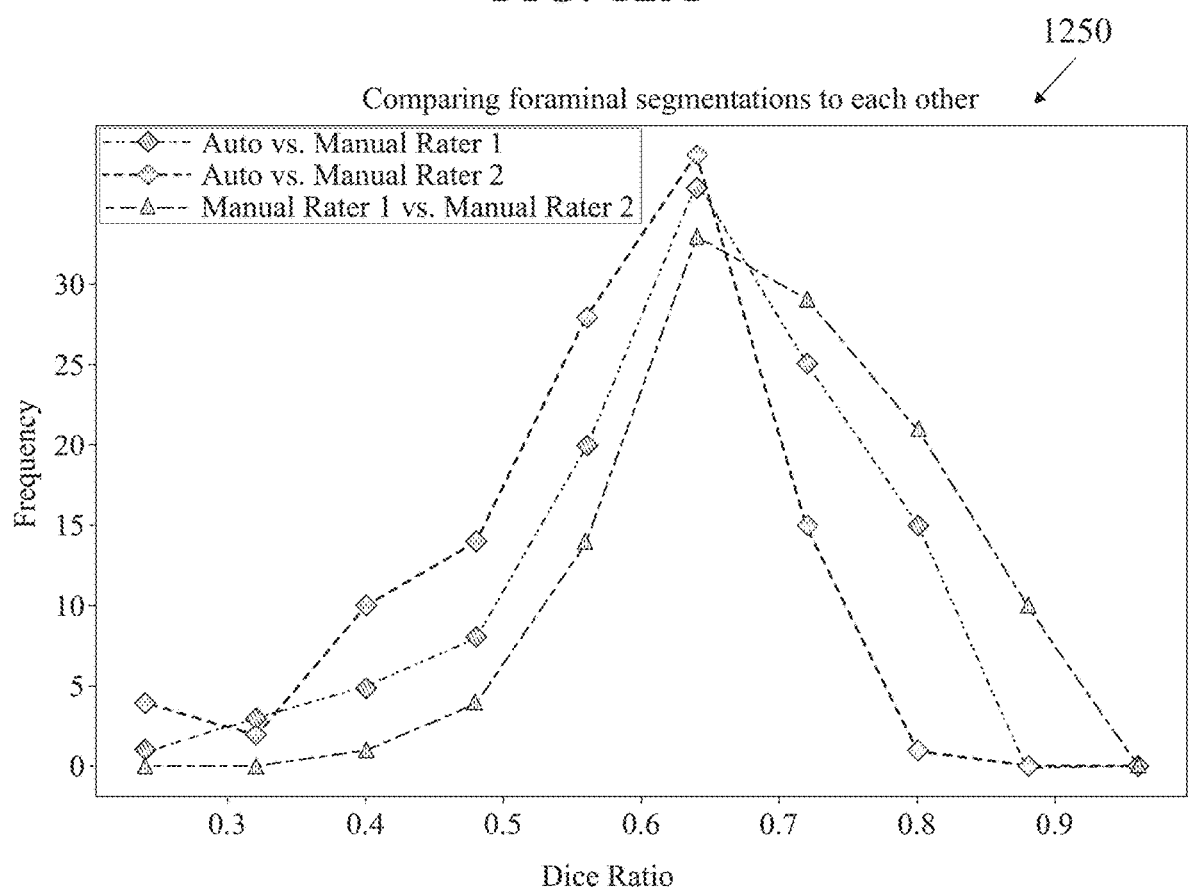
FIG. 12B is a graph for comparing foraminal segmentations to each other.

FIG. 12B compares the Dice scores of an automated model for segmentation versus two manual raters and with the Dice score of two manual raters compared to each other 1250 over multiple samples. In this example, the automatic segmentation is generally within a 0.1 difference of the manual rater comparisons. This comparison can be used to tune the model to meet or exceed human segmentations.

Figure 13A:
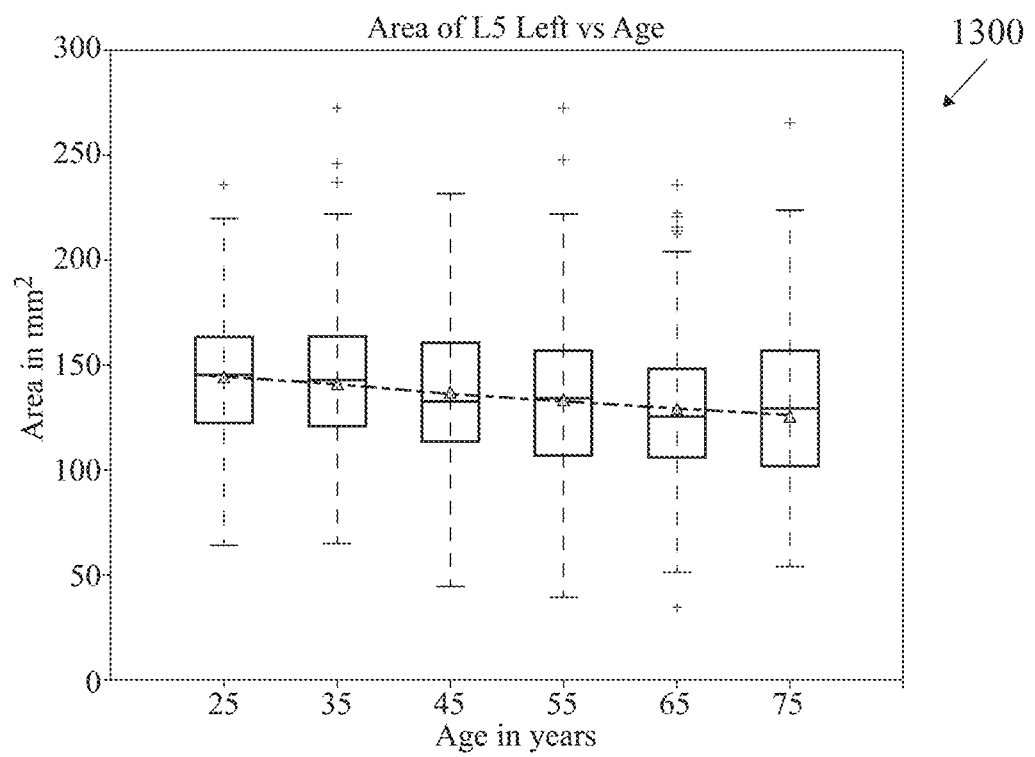
FIG. 13A is a graph of lumbar foraminal area decreasing with age based on data from a proprietary normal population.
Figure 13B:
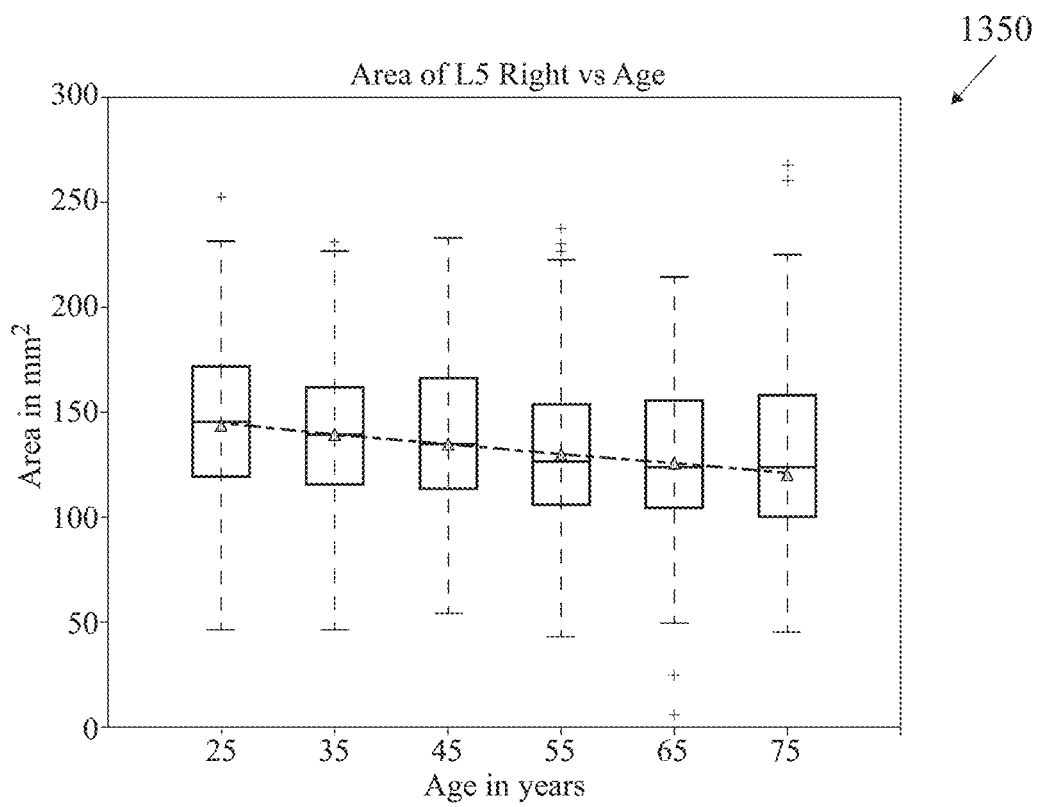
FIG. 13B is a graph of lumbar foraminal area decreasing with age based on data from a proprietary normal population.

FIG. 13A and FIG. 13B compare the left 1300 and right 1350 lumbar L5 neuroforamina areas of a normal population by age. The charts indicate that the average area of the L5 left and right lumbar neuroforamina decrease as people age. Since the narrowing of these areas may be used as indicators of surgical need, it's important to establish a normative area for specific ages.

Figure 14A:
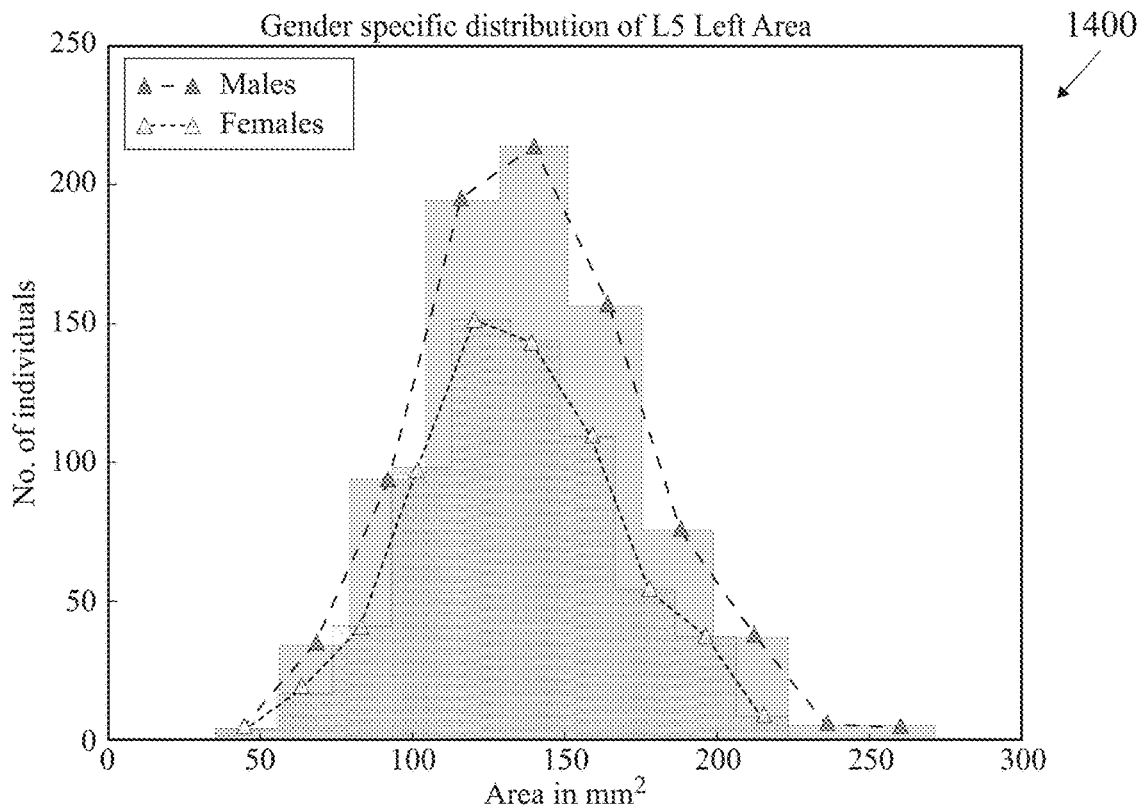
FIG. 14A is an image of graphs of gender specific distribution of the L5 left area.
Figure 14B:
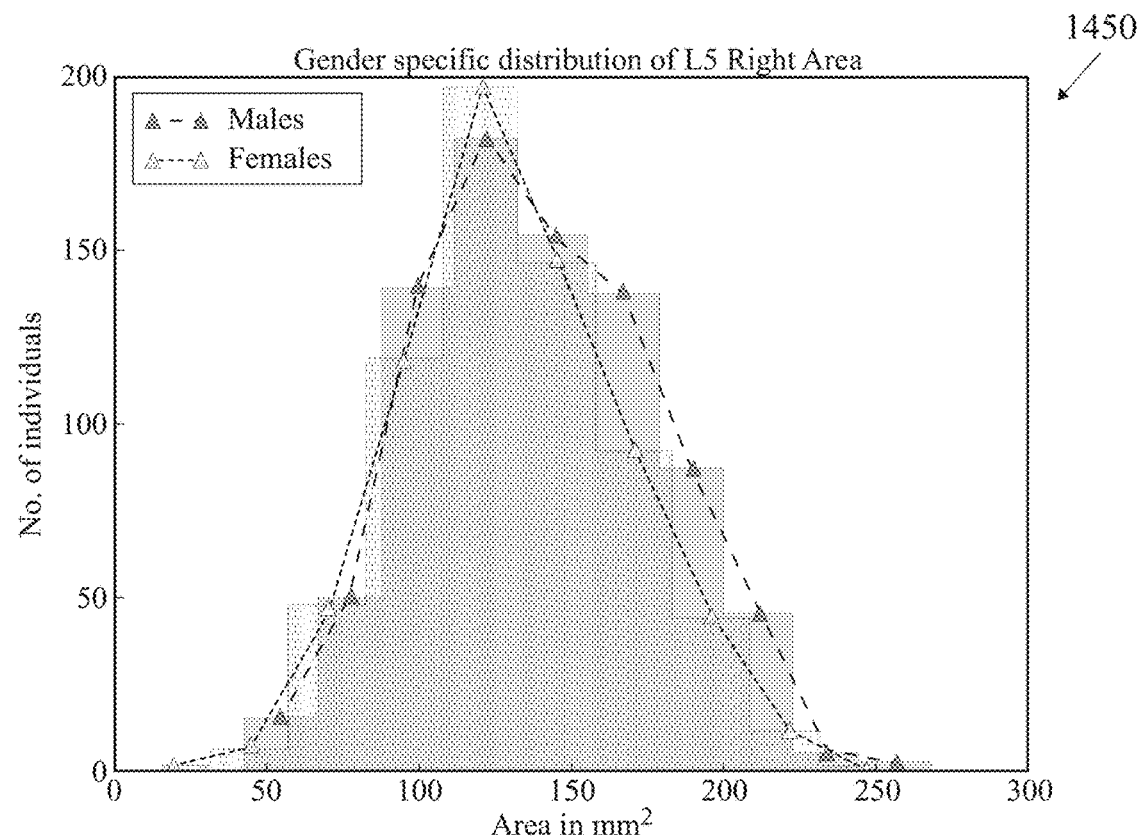
FIG. 14B is an image of graphs of gender specific distribution of the L5 right area.

FIG. 14A and FIG. 14B demonstrate the distribution in areas for the left 1400 and right 1450 lumbar L5 neuroforamina by gender. Similarly, to differences demonstrated for age, there is a significant difference in area by gender as well. As such, a model designed to indicate whether a specific area of the spinal anatomy was within or outside of the norm would need to factor in both age and gender in that determination.

Figure 15:
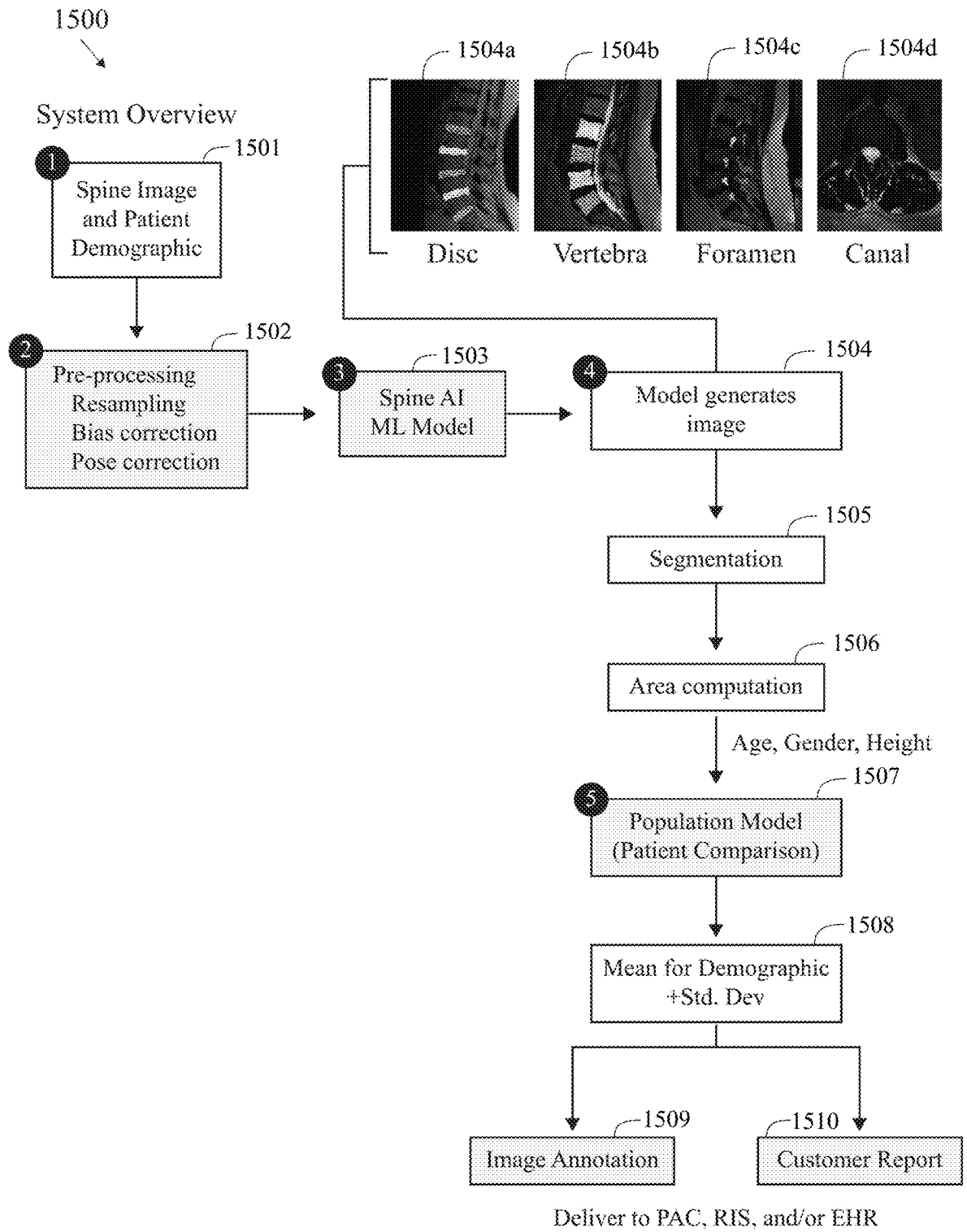
FIG. 15 is a flow chart of a method for generating a spine MRI report that includes an area computation, comparison to a normal population, and a standard deviation.

FIG. 15 illustrates one method for a system that intakes a patient MRI 1501 and outputs a report based on various computations 1509. The system performs a series of processing steps 1502 to optimize for running the model 1503 and to generate images 1504 and segmentation 1504 for each key anatomical area including discs 1504a, vertebra 1504b, foramen 1504c, and canal 1504d. The system then uses the segmentation 1505 to compute the area 1506. If age, gender, height are supplied 1507 they may be compared to the population model 1507 to compute comparison measures such as the standard deviation from the mean 1508. Finally, the system outputs the image annotation 1509 and a report characterizing the segmentations 1510. This report may be delivered to systems commonly deployed in health institutions such as a Picture Archiving and Communication System or an Electronic Health Record.

Figure 16A:
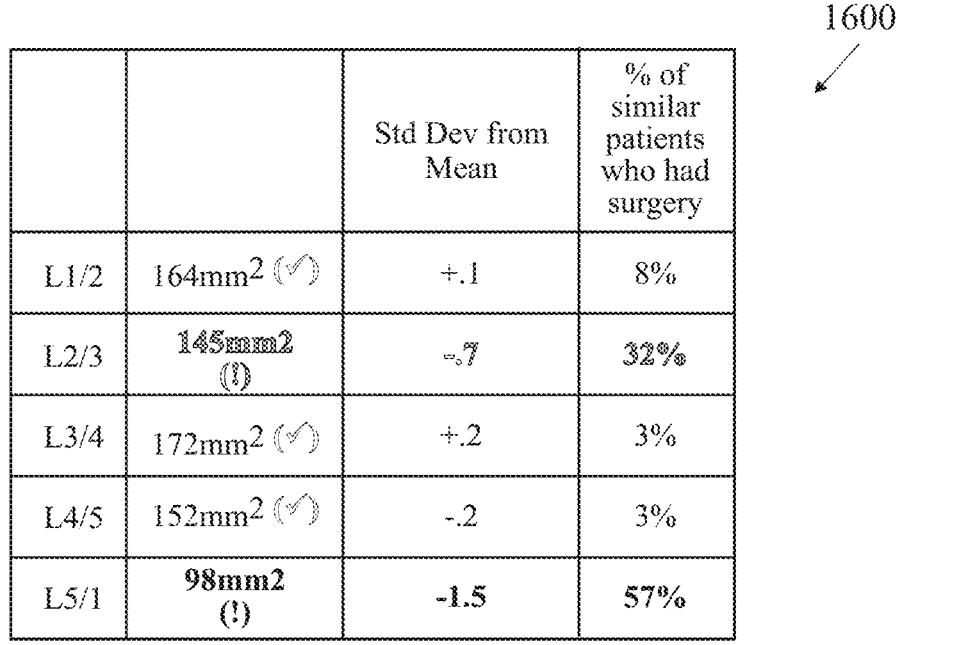
FIG. 16A is a table of data visualizations for each lumbar level.

FIG. 16A is a table showing one potential method of analyzing and displaying areas calculated by an automated segmentation mode 1600. The calculated areas may be shown along with their standard deviation from the mean to indicate the difference between the patient's anatomical area and that of an asymptomatic normal population. The areas could also be compared to a database that mapped the areas of similar patients to specific treatments undergone or that were deemed appropriate based on outcomes or other method. The system could thus determine a percentage likelihood of that specific treatment being delivered or appropriate (e.g. surgery or physical therapy or other).

FIG. 16B is another example view displaying how a given patient's anatomical areas compare to an established normal population by percentile range 1650. This view indicates an area range for each anatomical area aligned to a percentile range. The patient's measurement may be indicated as above or below the norm as well as severity using color coding, iconography, or other indicator. Finally, the table may display treatment statistics for similar patients such as a percentage likelihood of a given treatment or percentage likelihood of a positive outcome from a given treatment.

Figure 17:
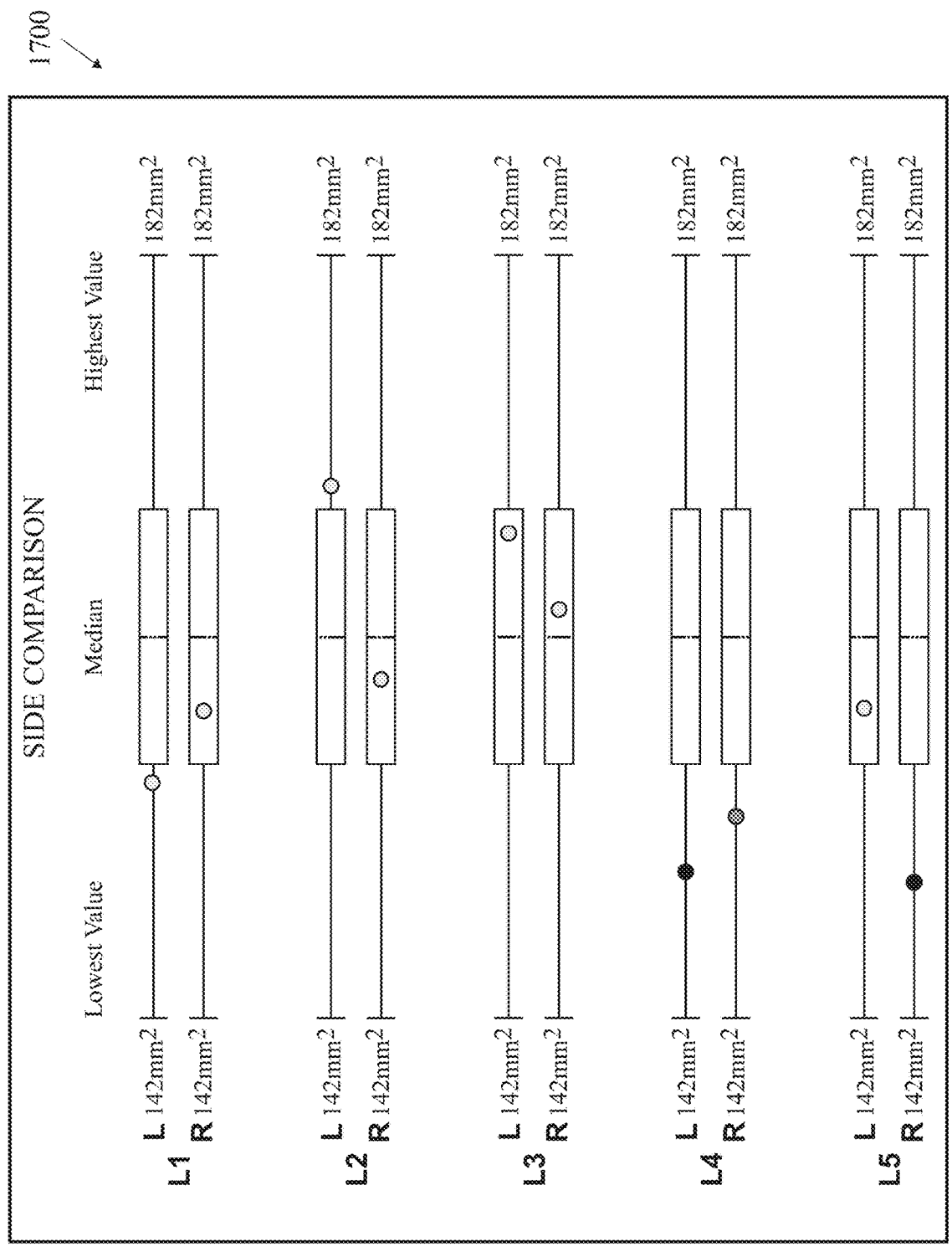
FIG. 17 is an illustration of area comparison to norm values for a demographic.

FIG. 17 is another example presentation of a patient's anatomical area as compared to an expected range for a similar patient 1700. In this view, the patient's measurement is indicated by a colored circle along a range. A rectangle in the center of the range shows the expected range with measurements to the left as below the norm and measurements to the right as above the norm.

FIG. 18 is table view that includes a threshold for a given treatment such as surgery aligned to the percentile ranges for anatomical areas 1800. This threshold could be set based on various criteria. In this example, the percentile is aligned to an improvement in Visual Analogue Score (VAS) after surgery. A VAS score is a commonly used Patient Reported Outcome Measure (PROM) recorded before and after surgery. In this example presentation, the patient's measurements are highlighted and include iconography to indicate when a patient is a candidate for the given treatment.

Figure 19A:
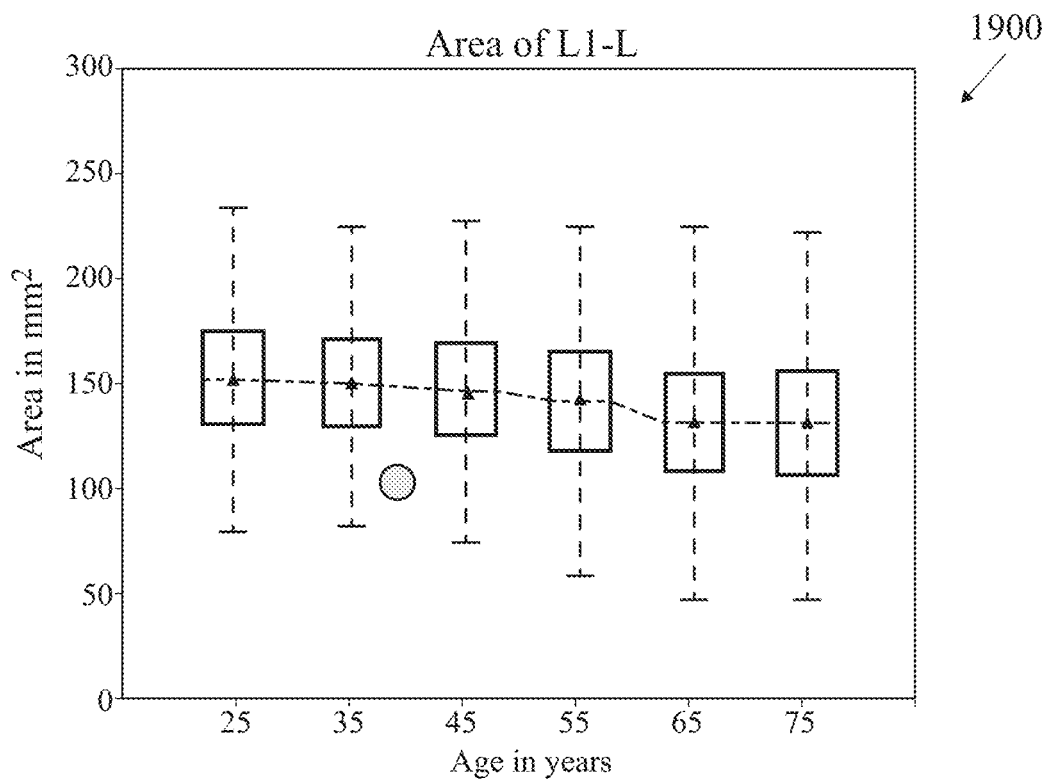
FIG. 19A is an illustration of area comparison to norm values by age.
Figure 19B:
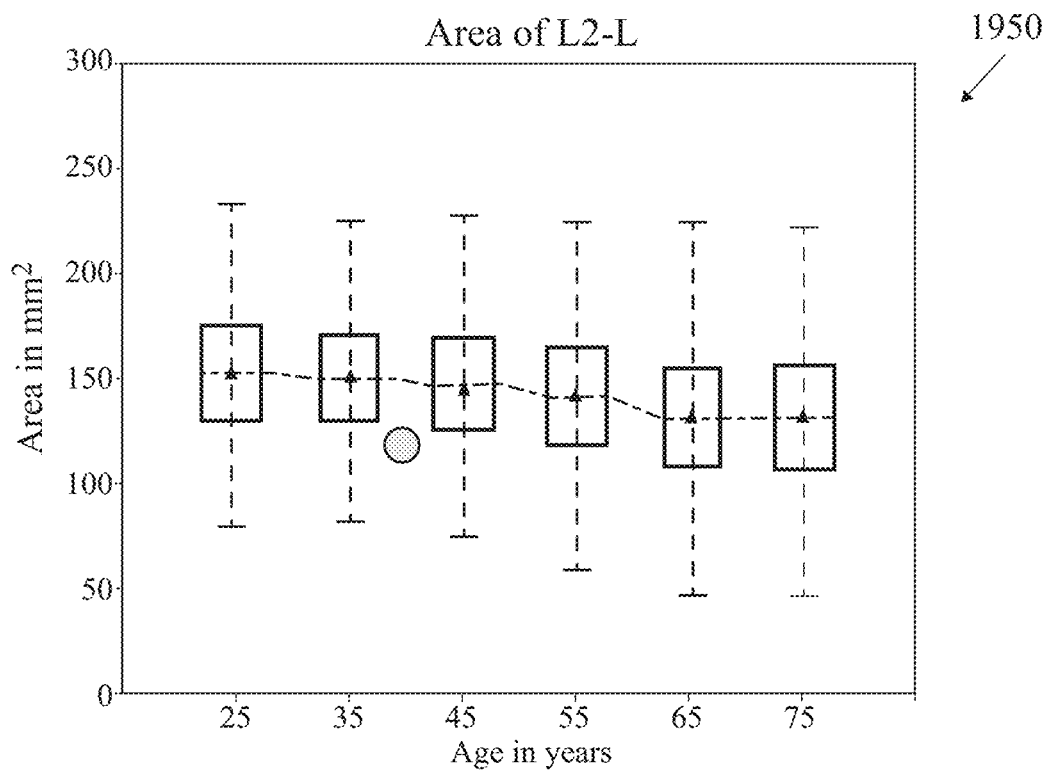
FIG. 19B is an illustration of area comparison to norm values by age.

FIG. 19A and FIG. 19B compare the left 1900 and right 1950 lumbar L2 neuroforamina areas of a normal population by age. The charts indicate that the average area of the L2 left and right lumbar neuroforamina decrease as people age. These figures show that a change in area as patients age can be generally established.

Figure 20:
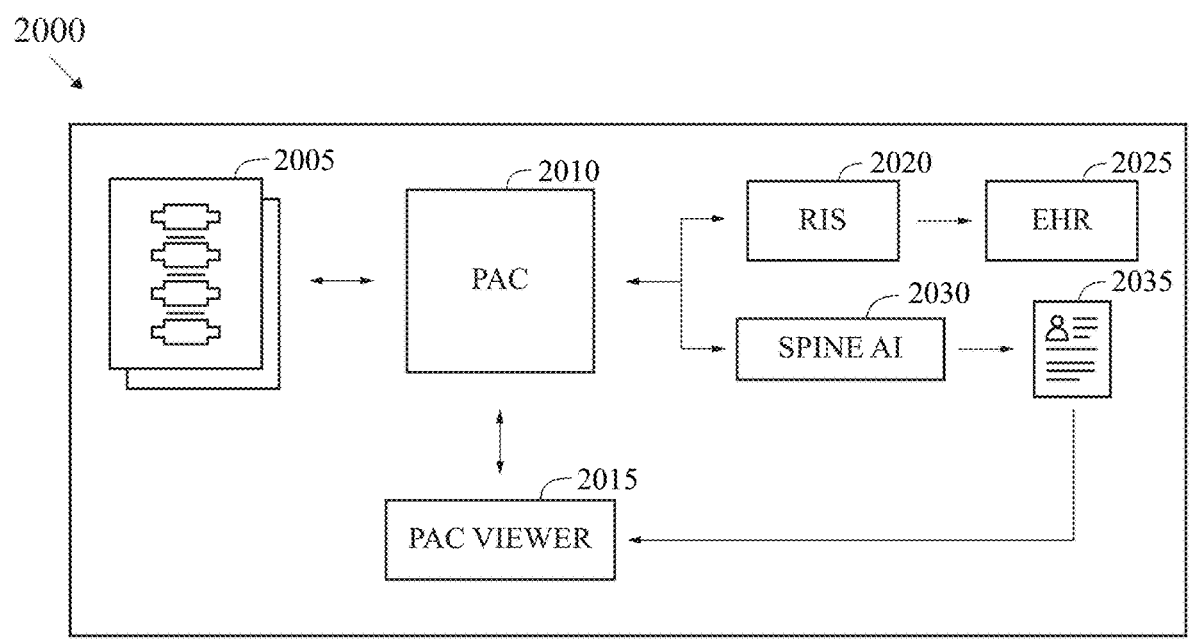
FIG. 20 is a block diagram of possible integration points for a clinical decision support system.

FIG. 20 is a diagram of possible integration points for a clinical decision support system 2000. In this diagram, the spine AI system integrates with a Picture Archiving System to retrieve patient images on a regular basis or when requested. The clinical decision support system processes the images and generates a report as a PDF, DICOM image, or other format and sends that file or a link to a file to other systems. The report may be sent to a Radiological Information System and/or the Electronic Health Record where it can be retrieved by physicians associated with a patient's care. Additionally, the report or annotated images can be viewed within the PACs by radiologists or other physicians associated with a patient's care.

Figure 21:
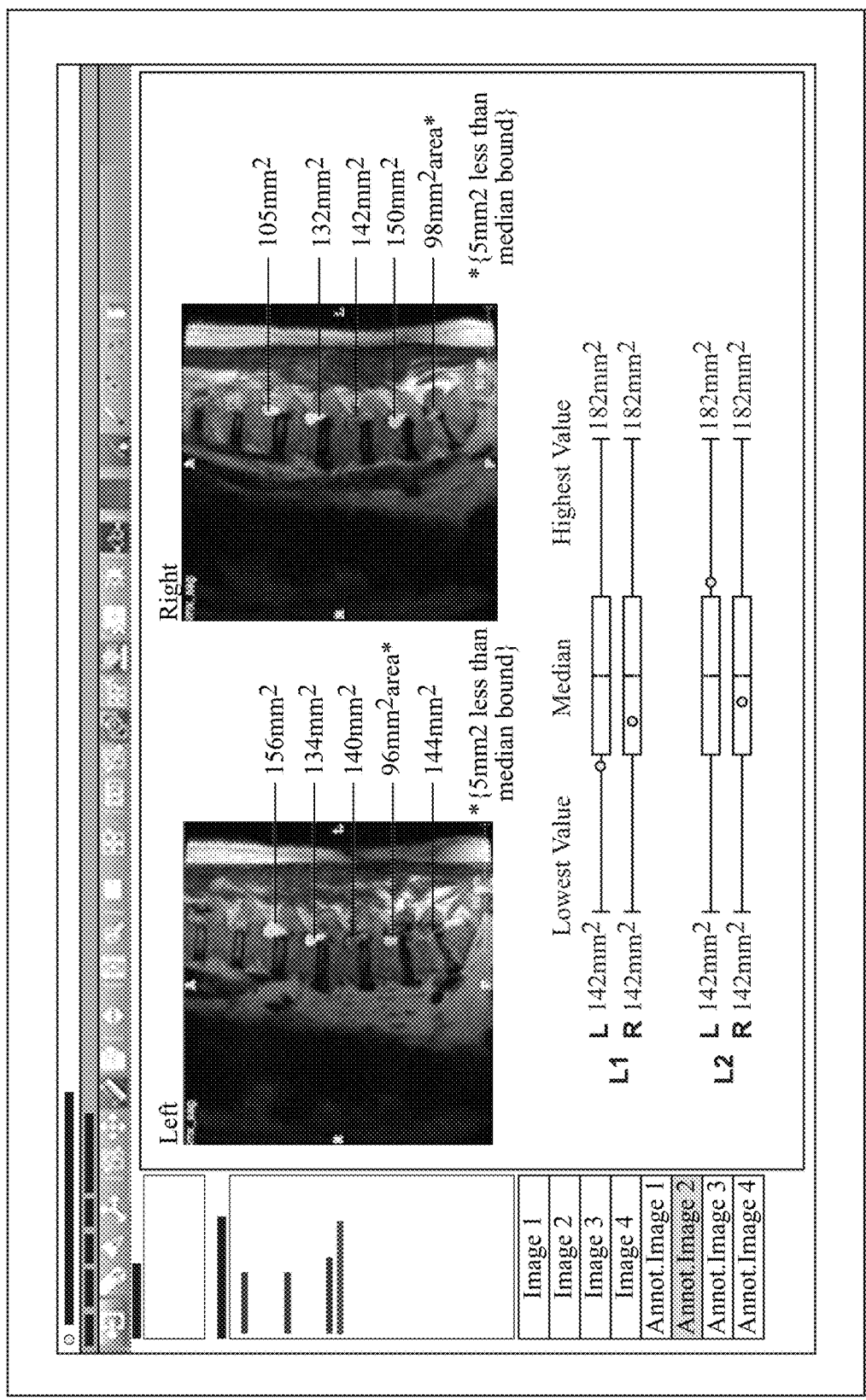
FIG. 21 is an example of a PACS integration view.

FIG. 21 is a conceptual view of a DICOM format image within a PACS viewer 2100. The image is annotated with various area measurements and calculations generated by a clinical decision support system utilizing a segmentation model. This invention allows a radiologist or other physician reviewing a patient's imaging to access automatically quantified areas, calculations using those areas, comparisons to a normative range, and other comparisons to a larger patient database. The conceptual image here also shows that the additional annotations can be made available in the traditional workflow of a radiologist or physician who is familiar with accessing a PACS viewer.

Figure 22:
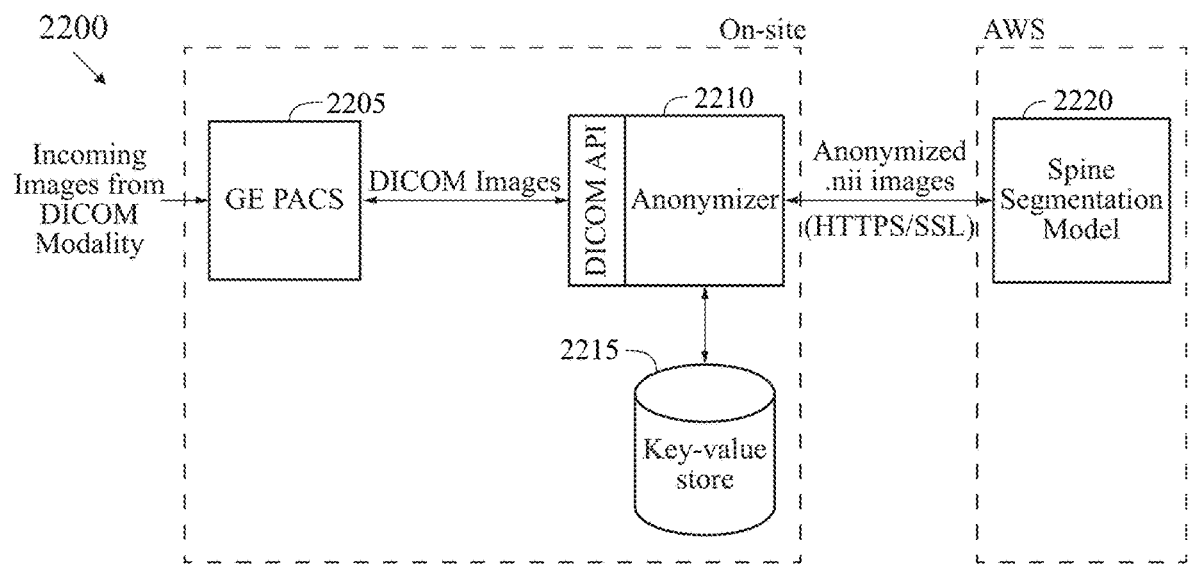
FIG. 22 is a block diagram of a PACS integration including an anonymizer between the institutions PHI data and the spine segmentation model.
Figure 23:
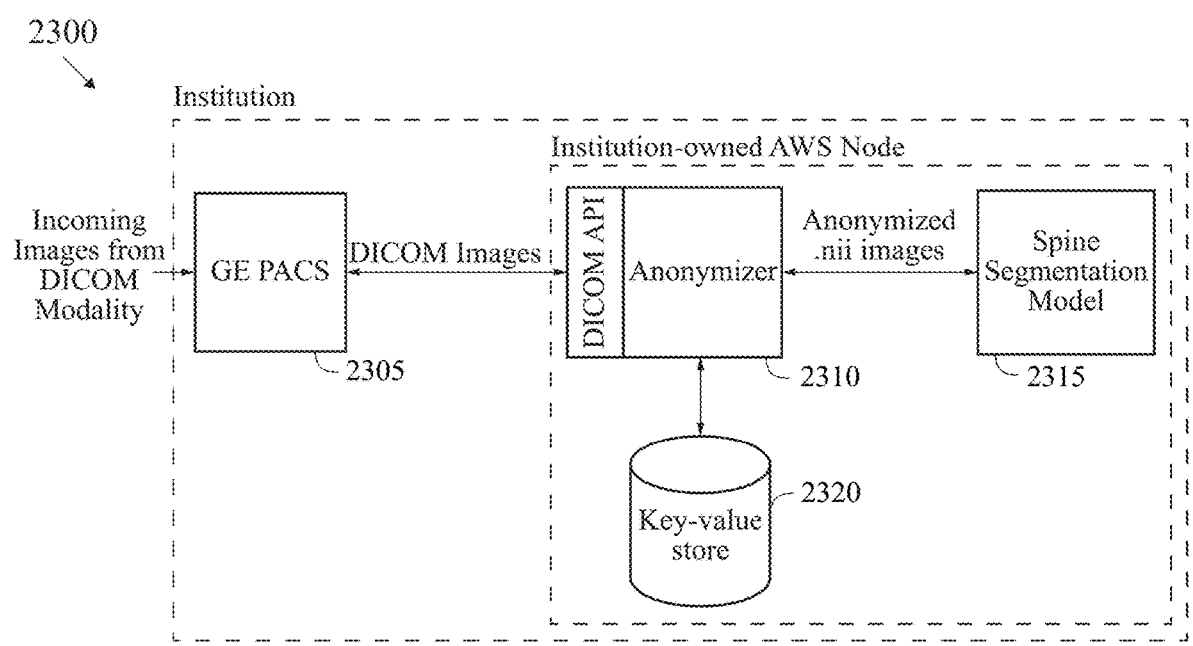
FIG. 23 is a block diagram of a PACS integration with an institution in which the spine segmentation model is housed entirely within institution owned infrastructure.

FIG. 22 and FIG. 23 are diagrams of architectures that would support a systems ability to retrieve images, anonymize those images, run segmentation algorithms, annotate images, and add them to the study for review in PAC viewer. FIG. 22 shows a segmentation system 2200 with incoming images in a DICOM format to a PACS system (e.g. GE Centricity) 2205. The images are passed to an anonymizer which removes all identifying information from the DICOM file 2210 and generates a key value for each study 2215. The study is then passed over HTTPS to a segmentation model hosted on cloud infrastructure such as Amazon S3, Google Cloud, Microsoft Azure or other 2220. When the model is finished running, the segmentations are fed back through the anonymizer which utilizes the key value store to attach the data measurements to the original DICOM studies in the PACS system. In this diagram, the Cloud infrastructure (e.g. AWS) is controlled by the provider of the trained segmentation model. FIG. 23 shows largely the same architecture 2300, but the Cloud infrastructure is owned by the institution running the software. The PACS system 2305, anonymizer 2310, key value store 2320, and spine segmentation model 2315 are all within the institutions infrastructure. This is desired in some cases so that the institution has full control over the security and privacy policies enabled by the infrastructure. In both cases, the anonymizer component is optional but is included in the diagram as it provides an additional layer of security and privacy for patient data by ensuring that the model provider has no access to Protected Health Information (PHI).

Figure 24:
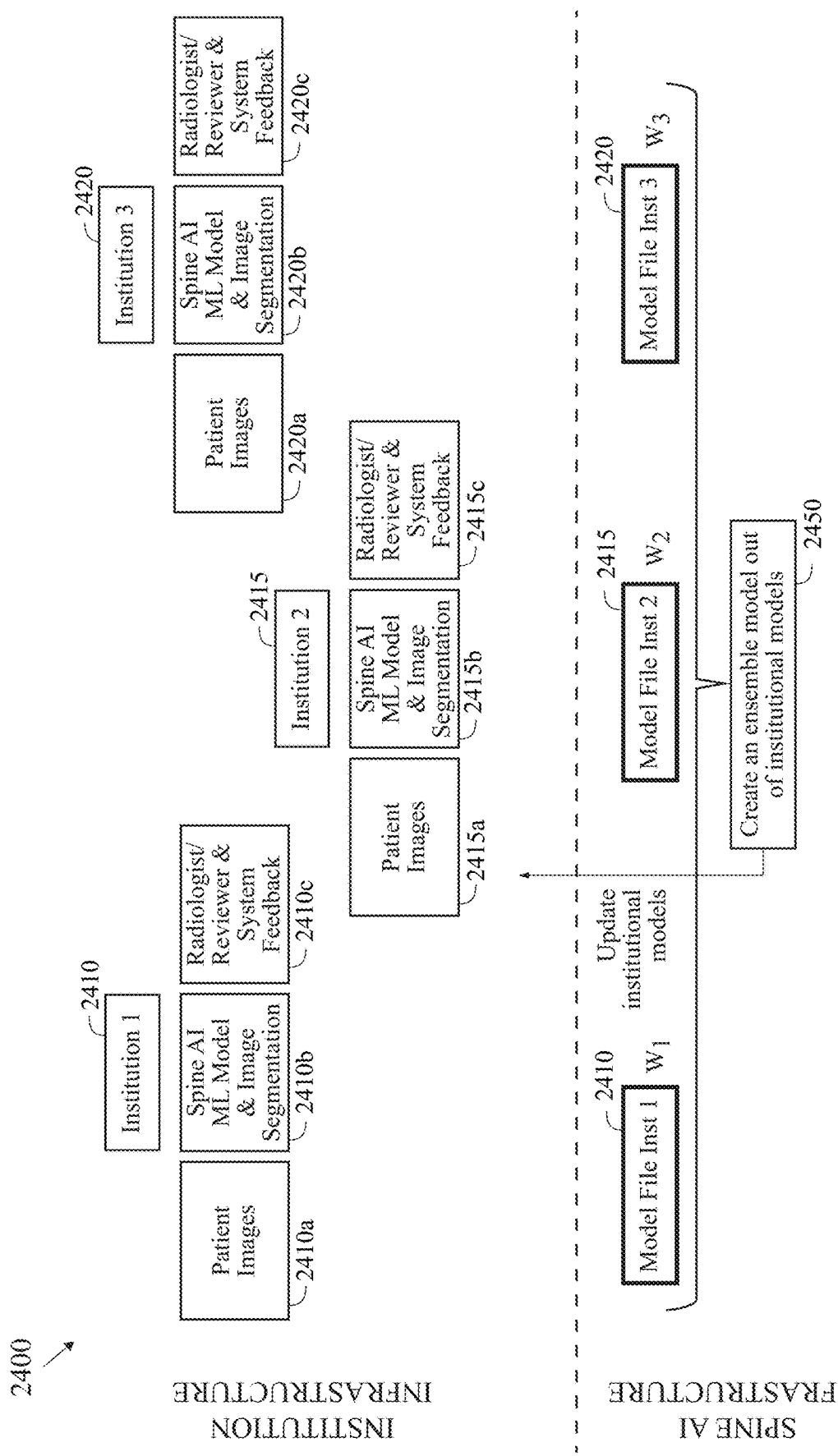
FIG. 24 is a flow chart of a method for updating a model across institutions where the spine model is housed locally, using an ensemble model of models trained at each institution.

A segmentation model could be improved over time based on feedback from the users of this model. However, if a clinical decision support system's imaging segmentation model is entirely housed within each institution's infrastructure, rather than in a single cloud instance, a challenge arises to codify the feedback into a single model. FIG. 24 shows one strategy for integrating model improvements from each segmentation model installation. The diagram shows a model unique to two or more institutions that is automatically improved based on system feedback 2400. In this example, Institution 1 2410 houses patient images 2410*a*, the spine AI model performing segmentation 2410*b*, and a system for inputting feedback as a user 2410*c*. Similarly, a second institution and third institution have implementations including these same components. For example, if the system at institution 2 2415 were to process a patient image 2415*a* utilizing the segmentation model 2415 and a radiologist were to flag an image as having an error or were to provide an additional manual segmentation 2415*c*, the model at that institution could be automatically retrained to incorporate this feedback. This could also occur at institution 3 2420 where perhaps patient image 2420*a* was segmented by the model instance unique to that institution 2420*b* and flagged as having a specific characteristic such as a symptom or treatment 2420*c*. So on and so forth, each institution could improve its model locally through user feedback. At some regularity, each institution's current model would be combined into an ensemble model. Lastly, the ensemble model could be pushed back as a new model version to the institutions so that they would benefit from the aggregated inputs.

Figure 25:
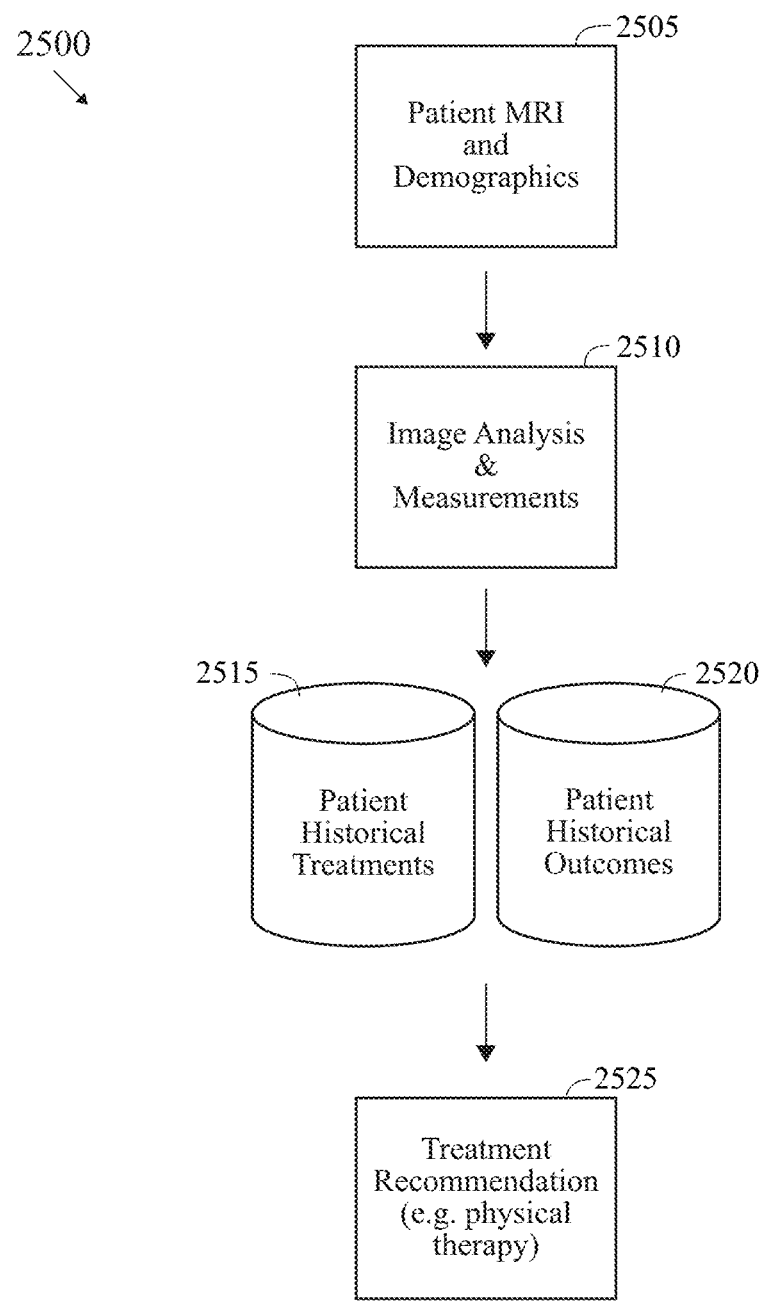
FIG. 25 is a diagram showing possible inputs for a treatment recommendation.

FIG. 25 describes a Clinical Decision Support system that provides a recommendation for a specific treatment (e.g. physical therapy) 2500. This system takes the patient MRI and demographic information (such as age, gender, height) 2505 as inputs to generate measurements and associated analysis 2510. These measurements are then compared to the historical treatments 2515 and outcomes data 2520 of other patients with similar measurements to provide a recommendation and degree of certainty 2525. As a simple example, if 100% of patients who had lumbar canal measurements 10-20% below the mean showed a 100% chance of improvement through physical therapy, a patient analyzed through the system would receive a recommendation for physical therapy with that confidence level (accounting for a statistically significant sample).

Figure 26:
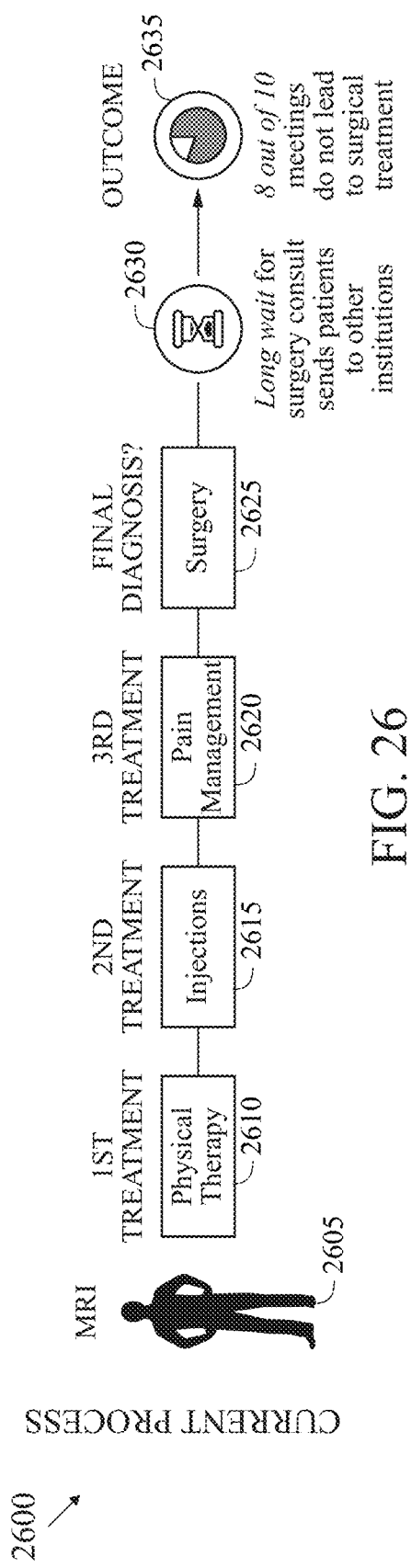
FIG. 26 is a flow chart of a prior art process for a patient with back pain as compared to the process with the automatic recommendation system.

FIG. 26 outlines a key problem this invention aims to solve 2600. Patients 2605 with back pain receive variable care and are often sent to multiple treatments such as physical therapy 2610, steroidal injections 2615, pain management 2620, or surgery 2625 before a treatment is identified that leads to an improved outcome. This results in extended wait times for care 2630, inefficient use of physician experts 2635, and even depression in some patients. As the diagram shows, at least 80% of surgical consultations do not result in the patient receiving a surgical intervention 2635. Additionally, longer wait times to resolve back pain are associated with depression and opioid use and an estimated 250,000+ surgeries happen annually that are unnecessary based on outcomes. In summary, this suggests an opportunity to use data to optimize which patients are referred to a given treatment or physician (whether surgeon, physical therapist, or other).

Figure 27:
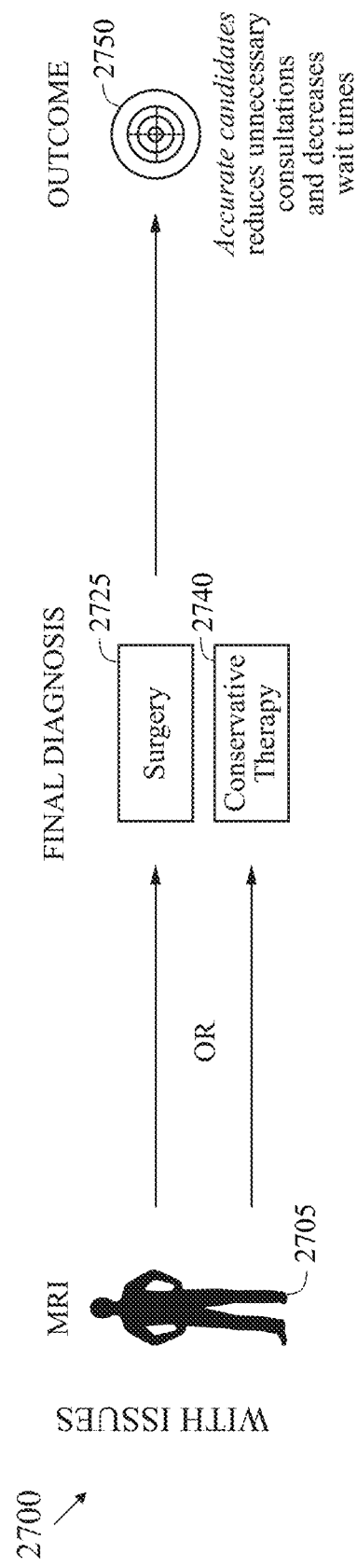
FIG. 27 illustrates a process in which a patient's MRI is analyzed by a computer model to provide a suggested diagnosis or treatment.

FIG. 27 describes a process 2700 in which a patient's MRI 2705 is analyzed by a computer model to provide a suggested diagnosis or treatment such as surgery 2725 or conservative therapy 2740. The measurements and treatment could be utilized by a primary care or other physician to make a more appropriate treatment referral resulting in more accurate candidates for each treatment including surgical intervention. In another iteration, the system itself could automatically make referrals based on a set of rules via email, text message, or other communication protocol. This would result in patients being more accurately and more efficiently referred to appropriate physicians or treatment 2750, thereby improving patient experience and outcome.

Figure 28:
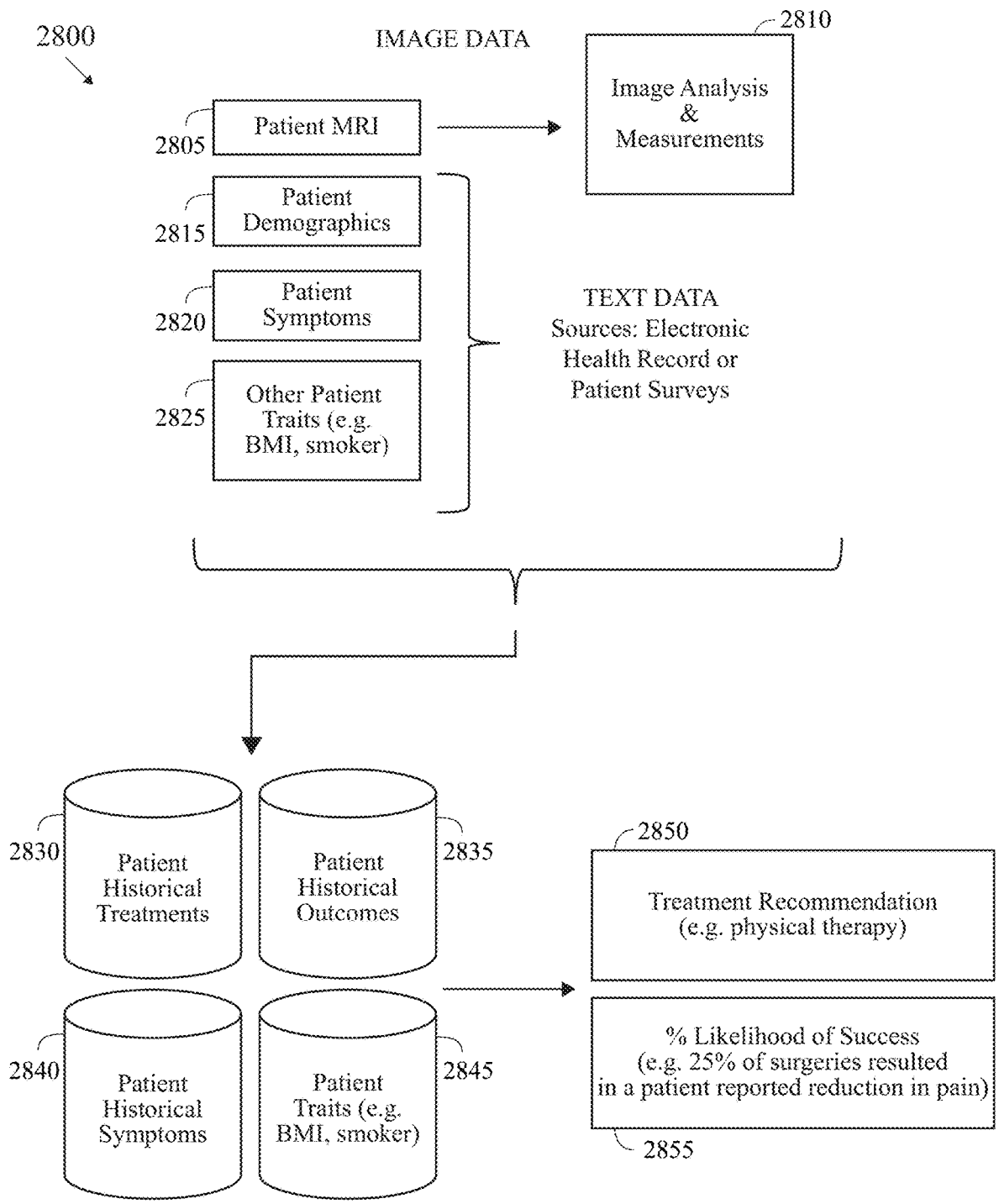
FIG. 28 is a flow chart showing the data inputs of a model that provides a treatment recommendation and likelihood of successful surgery.

FIG. 28 illustrates imaging and text inputs to a recommendation system 2800 including patient traits inputted or retrieved from patient surveys 2825 or Electronic Health Records 2820 with demographic information 2815 and imaging measurements and analysis 2810. Some studies have shown correlations with positive or negative outcomes in surgery with patient traits such as BMI or smoking. These inputs can be combined with imaging data to produce an overall score for the patient condition or an indication of surgical or other treatment appropriateness. In this system, a patients inputted data is compared to a historical database of treatments 2830, outcomes 2835, symptoms 2840, and traits (e.g. bmi, smoker, imaging measurements, etc) 2845 to find most similar patients and compute a treatment recommendation 2850 or likelihood of success for a given treatment 2855. This data could be analyzed through numerous computational methods that would be useful to get patients to an appropriate treatment such as through a utility matrix, nearest neighbor algorithm, or simple correlation measures.

Figure 29:
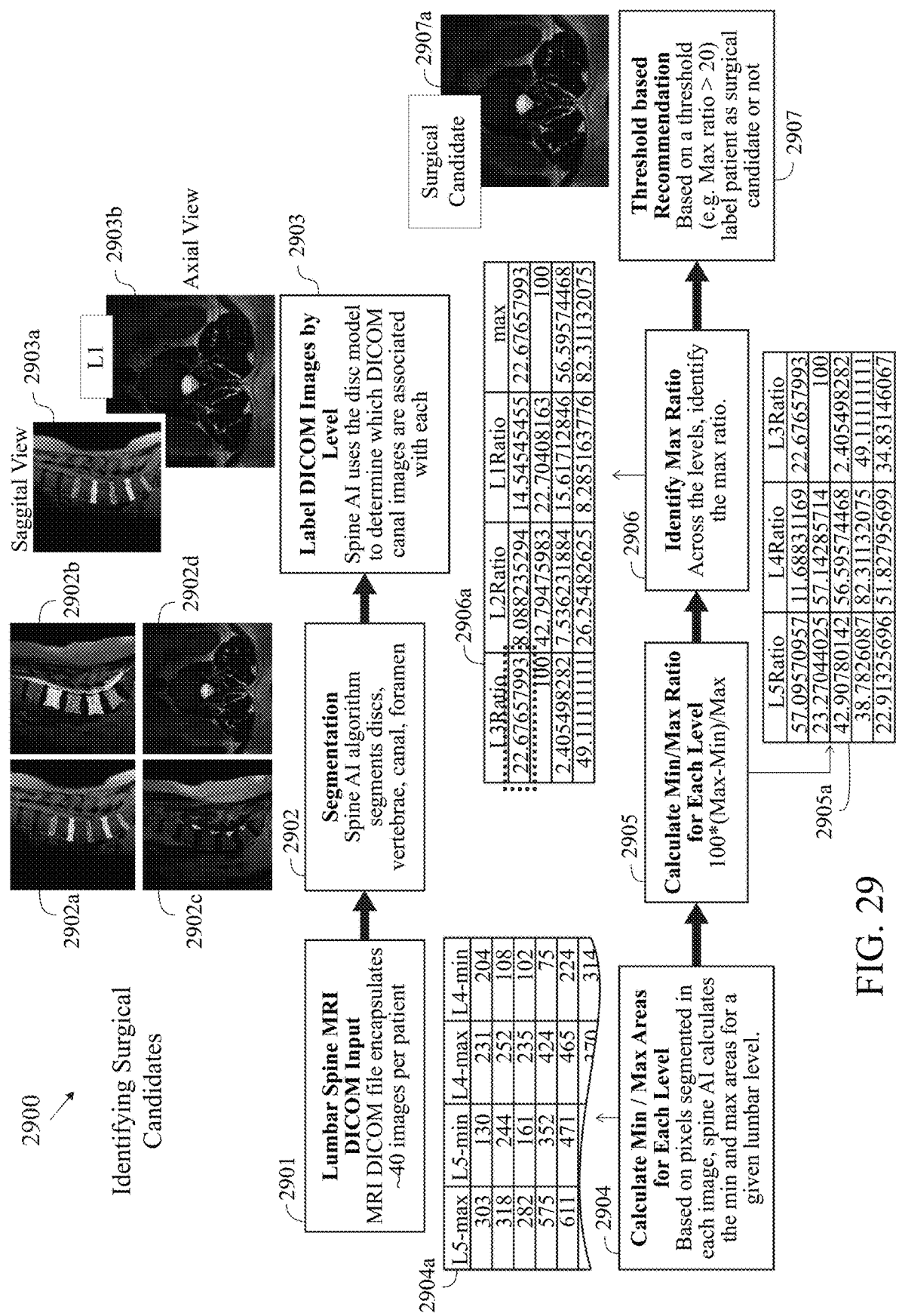
FIG. 29 is a flow chart showing an example of the present invention using only imaging data to recommend whether a patient is a surgical candidate.

FIG. 29 shows one method for delivering a treatment recommendation or surgical candidacy designation 2900. In this method, spine MRIs in DICOM format 2901 including axial and sagittal views showing the discs 2902a, vertebrae 2902b, foramen 2902c, and canal 2902d, are inputted into a segmentation model 2902 which automatically segments and labels the key anatomical areas 2903. The system recognizes the sequence placement of the discs (e.g. L1, L2, L3, etc) in the sagittal view 2903a and aligns this to the canal images in the axial view 2903b. This allows the system to identify a minimum and maximum area for the image slices 2904 near the given lumbar level and compute a min/max ratio for each level 2905. The partial table 2904a shows an example min/max for the L5 and L4 levels and partial table 2905a shows an example min/max ratio for L3, L4, and L5. Finally, partial table 2906a identifies the max ratio across levels 2906. Based on correlation with surgical data (e.g. patients who went to surgery, patients deemed appropriate for surgery, etc) or other decision criteria, a threshold can be set to label a patient as a surgical candidate or not 2907.

Figure 30:
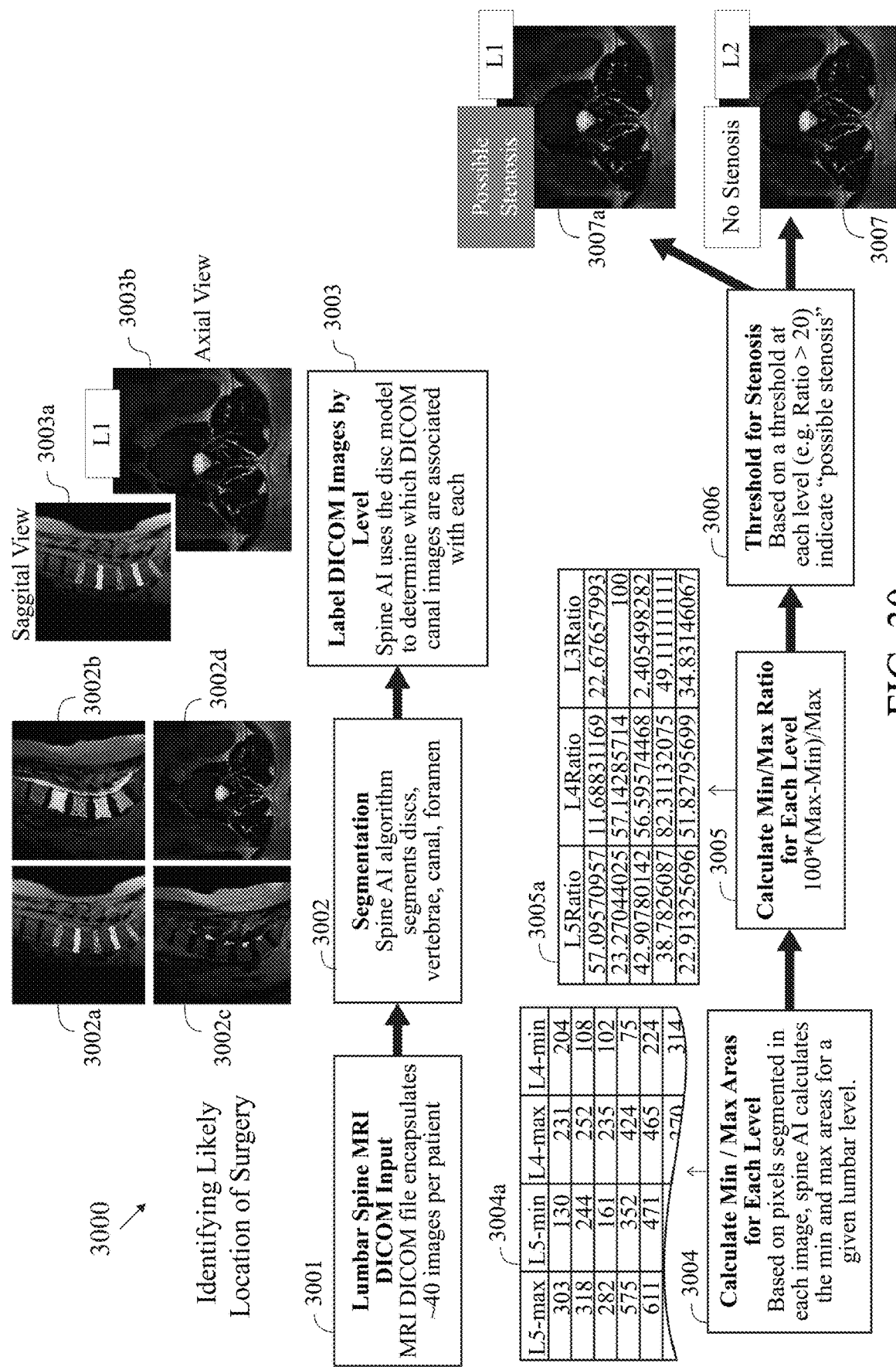
FIG. 30 is a flow chart showing a second example of the present invention using only imaging data to recommend whether a patient is a surgical candidate.

FIG. 30 shows the same input and processing scenarios as FIG. 29, but in this example a threshold his set for determining stenosis or surgical candidacy at a specific lumbar level (location) 3000. In this method, spine MRIs in DICOM format 3001 including axial and sagittal views showing the discs 3002a, vertebrae 3002b, foramen 3002c, and canal 3002d, are inputted into a segmentation model 3002 which automatically segments and labels the key anatomical areas 3003. The system recognizes the sequence placement of the discs (e.g. L1, L2, L3, etc) in the sagittal view 3003a and aligns this to the canal images in the axial view 3003b. This allows the system to identify a minimum and maximum area for the image slices 3004 near the given lumbar level and compute a min/max ratio for each level 3005. The partial table 3004a shows an example min/max for the L5 and L4 levels and partial table 3005a shows an example min/max ratio for L3, L4, and L5. A threshold can be set to label a given spinal level as exhibiting stenosis or not 3007. Further, a definition may be set to recommend surgical intervention at a given level based on the stenosis score rendered.

Figure 31:
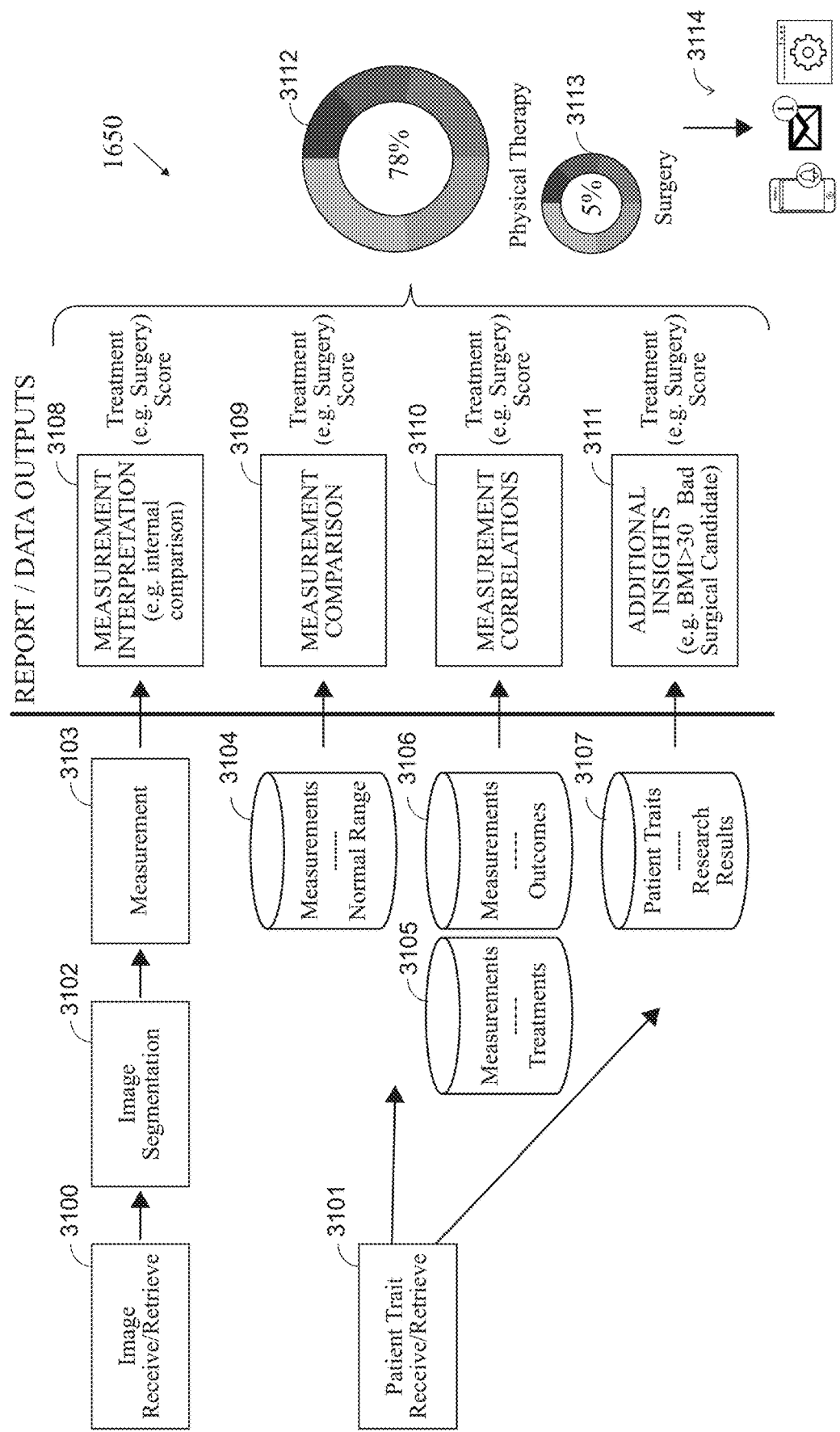
FIG. 31 shows an end to end system which intakes and segments images and patient profile data and then compares those relevant data to output a report with a weighted diagnosis and treatment recommendation.

FIG. 31 illustrates an end to end system that receives or retrieves images from a web interface upload, a PACs system or other 3100 and patient profile data from patient intake forms, electronic health records, medical or fitness monitors, or direct text input 3101. The images received are automatically segmented 3102 and areas of interested measured 3103.

The patient traits and spine feature measurements are compared with a database of normal measurement ranges 3104, treatments undergone by patients with similar measurements 3105, and optionally treatments with outcomes data undergone by patients with similar measurements 3106 to derive various comparison data.

The patient measurements can be interpreted independently through intrapatient comparisons 3109. For example, the system may identify narrowing (stenosis) in an area of the spinal canal by comparing an image slice to that of other nearby slices. Similarly, the system may measure cross-sectional area of lateral channel and cross-sectional area of dural sac and provide a ratio of these areas.

The patient measurements can be compared to a normal range for asymptomatic patients 3110 to output a measurement comparison such as a standard deviation from the norm. As an example, the system may compare the canal measurement or a disc measurement to a normal range to indicate stenosis or disc degeneration respectively.

The patient measurements can be compared to treatments and outcomes in a set of similar patients to derive a recommended treatment. For example, a higher percentage of patients with similar measurements that underwent surgical treatment and reported improvements in pain reduction such as through a Visual Analogue Score (VAS) could increase the likelihood of the system recommending that treatment.

Patient profile data is optionally compared with a database of profile data aligned to research results to generate additional insights 3111. As an example, BMI above 30 is known to have a correlation with a negative outcome in surgery.

Each of the data points derived by the system including measurement interpretations, measurement comparisons, measurement correlations, and profile-based insights can be weighted to calculate an overall recommendation score or percentage likelihood of success of a given treatment such as physical therapy 3112 or surgery 3113.

Success can be defined as a patient reporting a reduction in pain or being able to perform additional physical activities (e.g. walk further than prior to surgery).

Common measures include the Visual Analogue Scale and EQ5D. EQ-5D is a standardized instrument developed by the EuroQol Group as a measure of health-related quality of life that can be used in a wide range of health conditions and treatments.

The report or data points within a report can be sent to other systems such as email, phone, or other external system 3114. This may be used to expedite patient treatment or as part of a referral process.

Figure 32:
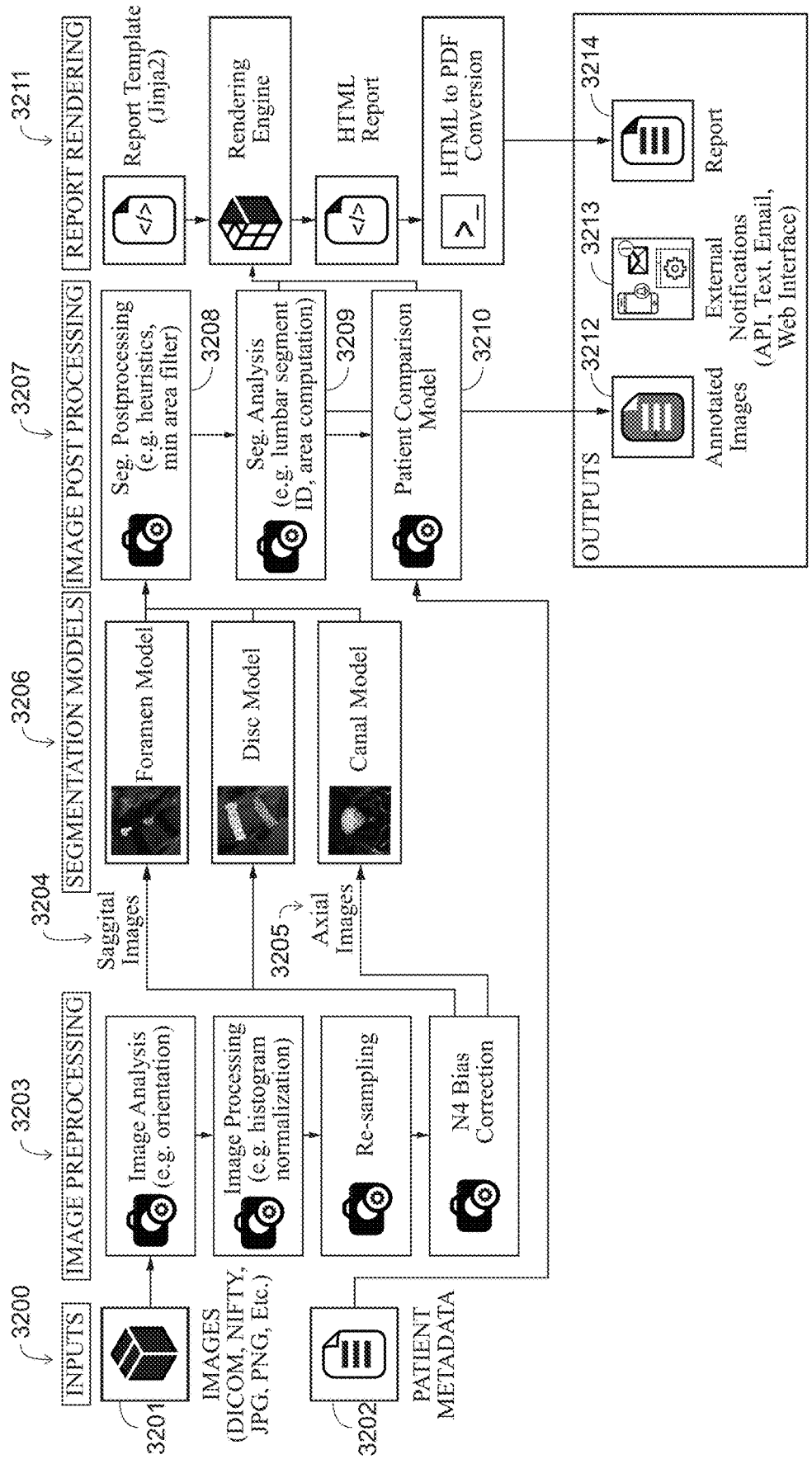
FIG. 32 shows another end to end system diagram with examples of image preprocessing, segmentation models, image post processing, report rendering, and outputs.

FIG. 32 shows an end to end system diagram. The system inputs 3200 include images in formats such as DICOM, NIFTY, JPG, or PNG 3201 and patient metadata via survey, electronic health record, or health monitor 3202. The image inputs go through a set of image preprocessing steps such as reorientation, histogram normalization, resampling, and bias correction 3203 to prepare the images for processing and distinguish sagittal 3204 from axial images 3205. Next, the system runs segmentation models for each area of interest such as the foramen, disc, canal, vertebra (3206). In image post processing 3207, the system runs various heuristics to ensure accuracy 3208, identifies segments in human readable ways (e.g. L1-5), computes areas 3209, and then runs the patient comparison model 3210 which compares the patient characteristics to a database of patient normative ranges, treatments, and outcomes 3210. The segmentation results and analysis, as well as the patient comparison results are outputted as image annotations 3212, as well as sent to the rendering engine as part of report rendering 3211. The report template produces HTML that is then converted to a PDF file of the final report 3214. The data or the report may be retrieved from the system via API or sent by the system to external systems such as API endpoints, text messaging systems, email systems, or web interfaces.

The system may be housed on cloud-based servers or run locally on a computer. The system may be packaged as a Docker container that can be deployed on cloud-based servers or locally on a computer.

An operating system controls the execution of other computer programs, running of the PSO platform, and provides scheduling, input-output control, file and data management, memory management, and communication control and related services. The operating system may be, for example Windows (available from Microsoft, Corp. of Redmond, Wash.), LINUX or other UNIX variants (available from Red Hat of Raleigh, N.C. and various other vendors), Android and variants thereof (available from Google, Inc. of Mountain View, Calif.), Apple OS X, iOS and variants thereof (available from Apple, Inc. of Cupertino, Calif.), or the like.

The method described in connection with the embodiments disclosed herein is preferably embodied directly in hardware, in a software module executed by a processor, or in a combination of the two. A software module preferably resides in flash memory, ROM memory, EPROM memory, EEPROM memory, RAM memory, registers, a hard disk, a removable disk, a CD-ROM, or any other form of storage medium known in the art. An exemplary storage medium is preferably coupled to the processor, so that the processor reads information from, and writes information to, the storage medium. In the alternative, the storage medium is integral to the processor. In additional embodiments, the processor and the storage medium reside in an Application Specific Integrated Circuit (ASIC). In additional embodiments, the processor and the storage medium reside as discrete components in a computing device. In additional embodiments, the events and/or actions of a method reside as one or any combination or set of codes and/or instructions on a machine-readable medium and/or computer-readable medium, which are incorporated into a computer software program.

In additional embodiments, the functions described are implemented in hardware, software, firmware, or any combination thereof. If implemented in software, the functions are stored or transmitted as one or more instructions or code on a computer-readable medium. Computer-readable media includes both computer storage media and communication media including any medium that facilitates transfer of a computer program from one place to another. A storage medium is any available media that is accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures, and that can be accessed by a computer. Also, any connection is termed a computer-readable medium. For example, if software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc", as used herein, include compact disc (CD), laser disc, optical disc, digital versatile disc (DVD), floppy disk and BLU-RAY disc where disks usually reproduce data magnetically, while discs usually reproduce data optically with lasers. Combinations of the above should also be included within the scope of computer-readable medium.

A computer program code for carrying out operations of the Present Invention is preferably written in an object oriented, scripted or unscripted programming language such as C++, C#, SQL, Java, Python, Javascript, Typescript, PHP, Ruby, or the like.

Each of the interface descriptions preferably discloses use of at least one communication protocol to establish handshaking or bi-directional communications. These protocols preferably include but are not limited to XML, HTTP, TCP/IP, Serial, UDP, FTP, Web Services, WAP, SMTP, SMPP, DTS, Stored Procedures, Import/Export, Global Positioning Triangulation, IM, SMS, MMS, GPRS and Flash. The databases used with the system preferably include but are not limited to MSSQL, Access, MySQL, Oracle, DB2, Open Source DBs and others. Operating system used with the system preferably include Microsoft 2010, XP, Vista, 200o Server, 2003 Server, 2008 Server, Windows Mobile, Linux, Android, Unix, I series, AS 400 and Apple OS.

The underlying protocol at a server, is preferably Internet Protocol Suite (Transfer Control Protocol/Internet Protocol ("TCP/IP")), and the transmission protocol to receive a file is preferably a file transfer protocol ("FTP"), Hypertext Transfer Protocol ("HTTP"), Secure Hypertext Transfer Protocol ("HTTPS"), or other similar protocols. The protocol at the server is preferably HTTPS.

Components of a server includes a CPU component, a graphics component, memory, non-removable storage, removable storage, Network Interface, including one or more connections to a fixed network, and SQL database(s). Included in the memory, is an operating system, a SQL server or other database engine, and computer programs/software.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the appended claims.

We claim as our invention the following:

1. A computer-implemented method for generating a diagnosis for a spinal disease, the method comprising:
   inputting a plurality of digital images of an axial plane of a patient's spine showing a plurality of successive points along a length of the spine;
   identifying a spinal canal or other spine anatomy in each image of the plurality of digital images;
   estimating a cross-sectional area of the spinal canal or spinal anatomy of interest in each image of the plurality of digital images;
   calculating a plurality of ratios by comparing the cross-sectional area in each image to the cross-sectional area in preceding images of the plurality of digital images; and
   generating a diagnosis for a spinal disease according to the plurality of ratios.

2. The method of claim 1, wherein a sagittal plane of a patient's spine is inputted and used to identify and measure cross-sectional areas.

3. The method of claim 1, wherein the medical diagnosis comprises a rating for a severity of spinal stenosis or related conditions.

4. The method of claim 1, wherein the diagnosis comprises a surgical evaluation or recommendation for surgical treatment of spinal stenosis or other spinal disease.

5. The method of claim 1, wherein the diagnosis comprises a recommendation for physical therapy treatment.

6. The method of claim 1, wherein the spinal anatomy is one of a spinal canal diameter, a spinal canal radius, or a spinal canal circumference.

7. The method of claim 1, further comprising calculating a plurality of differences, calculated by subtracting the previous spinal canal area from the current spinal canal area.

8. The method of claim 1, wherein one or more cross-sectional areas are compared to a sample population to output a degree of difference.

9. The method of claim 1, wherein one or more cross-sectional areas are compared to a to those of a comparison group to form aspects of a diagnosis.

10. The method of claim 9, wherein the comparison group is matched to the patient's demographics and health data.

11. The method of claim 1, wherein data relating to a formed medical diagnosis is sent to one or more external systems.

12. A non-transitory computer-readable medium that stores a program that causes a processor to perform functions to analyze a spine image by executing the following steps:

inputting a plurality of digital images of an axial plane of a patient's spine showing a plurality of successive points along a length of the spine;

identifying a spinal canal or other spine anatomy in each image of the plurality of digital images;

estimating a cross-sectional area of the spinal canal or spinal anatomy of interest in each image of the plurality of digital images;

calculating a plurality of ratios by comparing the cross-sectional area in each image to the cross-sectional area in preceding images of the plurality of digital images, or calculating a plurality of differences by subtracting a previous spinal canal area from a current spinal canal area;

generating a diagnosis for a spinal disease according to the plurality of ratios or the plurality of differences.

13. The non-transitory computer readable medium according to claim 12, wherein the diagnosis comprises a rating for a severity of spinal stenosis or related conditions.

14. The non-transitory computer readable medium according to claim 12, wherein the diagnosis comprises a surgical evaluation or recommendation for surgical treatment of spinal stenosis or related conditions.

15. The non-transitory computer readable medium according to claim 12, wherein the diagnosis comprises a recommendation for physical therapy treatment of spinal stenosis or related conditions.

16. The non-transitory computer readable medium according to claim 12, wherein the spinal canal area is replaced with a spinal canal diameter, a spinal canal radius, a spinal canal circumference, or other measurement correlated to the spinal canal area.

17. The non-transitory computer readable medium according to claim 12, wherein the diagnosis is formed according to the plurality of ratios.

* * * * *